(12) United States Patent
Arima et al.

(10) Patent No.: US 10,987,254 B2
(45) Date of Patent: Apr. 27, 2021

(54) APPARATUS AND METHOD FOR MANUFACTURING ABSORPTIVE ARTICLE

(71) Applicant: ZUIKO CORPORATION, Settu (JP)

(72) Inventors: Takashi Arima, Settu (JP); Miyuki Takanami, Settu (JP)

(73) Assignee: ZUIKO CORPORATION, Settu (JP)

( * ) Notice: Subject to any disclaimer, the term of this patent is extended or adjusted under 35 U.S.C. 154(b) by 0 days.

(21) Appl. No.: 16/763,048

(22) PCT Filed: Nov. 16, 2018

(86) PCT No.: PCT/JP2018/042587
§ 371 (c)(1),
(2) Date: May 11, 2020

(87) PCT Pub. No.: WO2019/098354
PCT Pub. Date: May 23, 2019

(65) Prior Publication Data
US 2020/0383840 A1 Dec. 10, 2020

(30) Foreign Application Priority Data
Nov. 17, 2017 (JP) .............................. JP2017-222260

(51) Int. Cl.
*A61F 13/15* (2006.01)
*B65G 47/84* (2006.01)
(Continued)

(52) U.S. Cl.
CPC ...... *A61F 13/15764* (2013.01); *B65G 47/848* (2013.01); *B65G 47/915* (2013.01); *B65H 5/12* (2013.01); *B65H 2701/1924* (2013.01)

(58) Field of Classification Search
CPC ............ A61F 13/15764; B65G 47/848; B65G 47/915; B65H 5/12; B65H 2701/1924; B65H 2801/57
See application file for complete search history.

(56) References Cited

U.S. PATENT DOCUMENTS 6,648,122 B1 * 11/2003 Hirsch ................. B65G 47/848
156/552
7,398,870 B2 * 7/2008 McCabe .................. B65H 5/12
198/377.08
(Continued)

FOREIGN PATENT DOCUMENTS

EP       2 374 437 B1      4/2016
JP    2002-301679 A       10/2002
(Continued)

OTHER PUBLICATIONS

PCT/ISA/210, "International Search Report for International Application No. PCT/JP2018/042587," dated Feb. 5, 2019.

*Primary Examiner* — Gene O Crawford
*Assistant Examiner* — Keith R Campbell
(74) *Attorney, Agent, or Firm* — Manabu Kanesaka

(57) ABSTRACT

An apparatus and method for manufacturing an absorptive article are capable of suppressing the occurrence of wrinkles in a constituent element of the absorbing article when transferring the constituent element to a downstream conveying device. A main suction pad that moves along a cylindrical or conical first virtual path surface receives a constituent element from an upstream conveying device, changes the orientation by 90° and conveys the constituent element to a second position. Sub-suction surfaces of the first and second sub-suction pads move around a second reference center line along a cylindrical or conical second virtual path surface centered on the second reference center line, while being aligned with each other with a space therebetween, suction end portions of the constituent element at the second position, and transfer the constituent element to the downstream conveying device at a third position.

8 Claims, 10 Drawing Sheets

(51) Int. Cl.
*B65H 5/12* (2006.01)
*B65G 47/91* (2006.01)

(56) References Cited

U.S. PATENT DOCUMENTS

| | | | |
|---|---|---|---|
| 9,248,053 B2 * | 2/2016 | Ogasawara | ........... A61F 13/496 |
| 2002/0112939 A1 | 8/2002 | Sumi et al. | |
| 2018/0140471 A1 | 5/2018 | Sato | |

FOREIGN PATENT DOCUMENTS

| | | |
|---|---|---|
| JP | 2010-142415 A | 7/2010 |
| WO | 2016/170940 A1 | 10/2016 |

* cited by examiner

Fig. 4
(a)
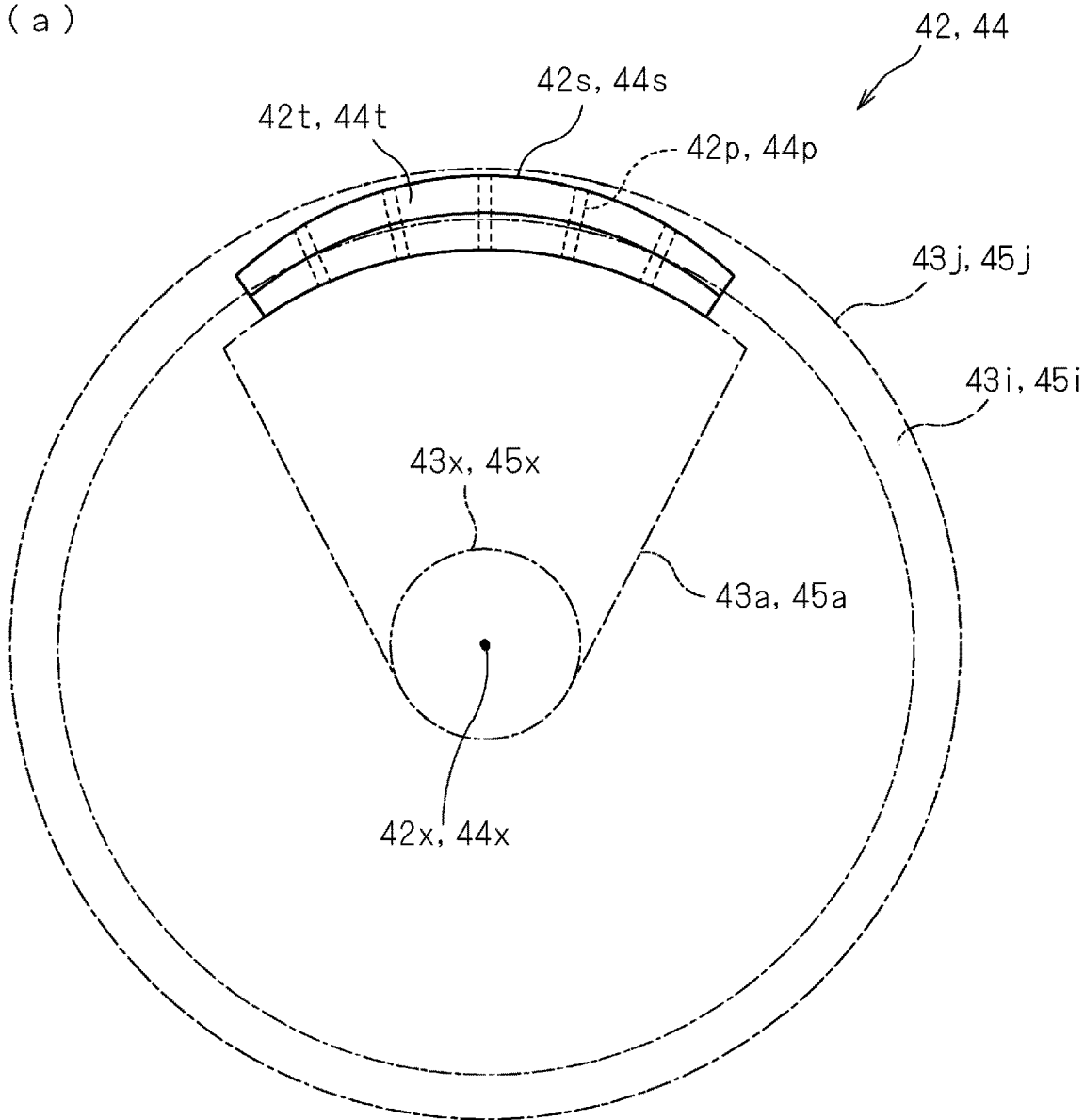
(b)
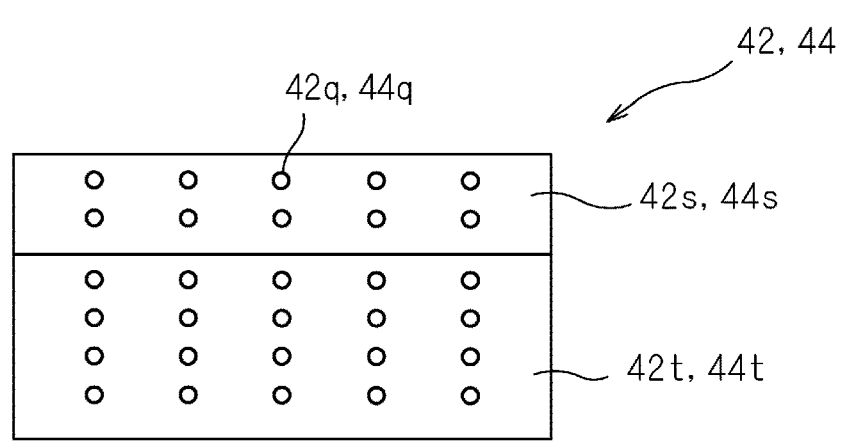

--Priar Art--

APPARATUS AND METHOD FOR MANUFACTURING ABSORPTIVE ARTICLE

RELATED APPLICATIONS

The present application is National Phase of International Application No. PCT/JP2018/042587 filed Nov. 16, 2018, and claim a priority from Japanese Application No. 2017-222260, filed Nov. 17, 2017, the disclosures of which are hereby incorporated by reference herein in its entirety.

TECHNICAL FIELD

The present invention relates to an apparatus and a method for manufacturing absorptive article and in detail, relates to an apparatus and a method for manufacturing absorptive article by which a constituent element of an absorptive article is received from an upstream conveying device and the constituent element is changed in orientation and thereupon transferred to a downstream conveying device.

BACKGROUND ART

In manufacturing of an absorptive article such as a disposable diaper or disposable shorts, etc., an apparatus for manufacturing absorptive article that receives a constituent element of an absorptive article from an upstream conveying device and after changing an orientation of the constituent element during conveying, transfers it to a downstream conveying device is used.

FIG. 10 is a schematic diagram showing an arrangement of a manufacturing apparatus 101 that is an example of such an apparatus. As shown in FIG. 10, with the manufacturing apparatus 101, suction pads 102 move in a direction indicated by an arrow R and change in orientation during movement. Each suction pad 102 receives a vertically oriented constituent element N conveyed by an upstream conveying device 111 at a receiving position RP, changes in orientation by 90° by rotating around a support shaft 103 while suctioning and conveying the received constituent element N to a transfer position SP, and transfers the horizontally oriented constituent element N to a downstream conveying device 112 at the transfer position SP. The suction pad 102 has a suction surface with an arcuate surface shape, that is, with an arcuately curved cross section like a portion of a cylindrical surface of predetermined angular range and this suction surface successively approaches and suctions from one end Nf to another end Nb of the constituent element N at the receiving position RP (see, for example, Patent Literature 1)

CITATION LIST

Patent Literature

Patent Literature 1: Japanese Published Unexamined Patent Application No. 2002-301679

SUMMARY OF INVENTION

Technical Problem

By such an arrangement, the suction surface is put in as close contact as possible with the constituent element at the receiving position RP to suppress occurrence of wrinkles in the constituent element during receiving.

However, with the above arrangement, the orientation of the suction pad 102 is changed and, at the transfer position SP, gaps with respect to the horizontally oriented constituent element N that is suctioned on the suction surface of arcuate surface shape form at both sides in an axial direction of a rotating drum of the downstream conveying device 112 and become a cause of occurrence of wrinkles in the constituent element N during transfer. The occurrence of wrinkles during transfer is especially significant when an elastic member is disposed in the constituent element N.

In view of the above actual circumstances, a problem that the present invention attempts to solve is to provide an apparatus and a method for manufacturing absorptive article that are capable of suppressing occurrence of wrinkles in a constituent element of the absorptive article when transferring the constituent element to a downstream conveying device.

Solution to Problem

To solve the above problem, the present invention provides an apparatus for manufacturing absorptive article arranged as follows.

An apparatus for manufacturing absorptive article receives a constituent element of an absorptive article from an upstream conveying device and after changing an orientation of the constituent element during conveying, transfers it to a downstream conveying device. The apparatus for manufacturing absorptive article includes (a) a main suction pad having a main suction surface curved to an arcuate surface shape between one end and another end and disengageably suctioning the constituent element, the main suction surface passing a first position and a second position by moving along a cylindrical or conical first virtual path surface centered on a first reference center line and in a circumferential direction of the first virtual path surface, the first virtual path surface being adjacent to the upstream conveying device at the first position, a reference direction connecting the one end and the other end of the main suction surface changing in orientation with respect to the circumferential direction of the first virtual path surface while the main suction surface moves, the reference direction being parallel to the circumferential direction of the first virtual path surface when the main suction surface passes the first position, and the reference direction being perpendicular to the circumferential direction of the first virtual path surface when the main suction surface passes the second position, (b) a first sub-suction pad having a first sub-suction surface disengageably suctioning a portion of the constituent element, the first sub-suction surface passing the second position and a third position by moving around a second reference center line and along a cylindrical or conical second virtual path surface centered on the second reference center line, the second virtual path surface being adjacent to the first virtual path surface at the second position and being adjacent to the downstream conveying device at the third position, and (c) a second sub-suction pad having a second sub-suction surface disengageably suctioning another portion of the constituent element, the second sub-suction surface passing the second position and the third position at the same time as the first sub-suction surface by moving around the second reference center line and along the second virtual path surface while being aligned with the first sub-suction surface with a space therebetween. Arrangements are made such that at the second position, the main suction surface of the main suction pad mutually approaches or contacts the first sub-suction surface of the first sub-suction pad and the second sub-suction surface of the second sub-suction pad and the space between the first sub-suction surface and the second sub-suction surface when the first sub-suction surface and the second sub-suction surface pass the third position becomes greater than the space between the first sub-suction surface and the second sub-suction surface when the first sub-suction surface and the second sub-suction surface pass the second position.

In the above arrangement, the main suction pad, with the main suction surface approaching or contacting the constituent element conveyed by the upstream conveying device when the first main suction surface passes the first position, suctions the constituent element onto the main suction surface and thereafter moves to the second position with the constituent element still being suctioned on the main suction surface. When the main suction surface passes the second position, the first sub-suction pad and the second sub-suction pad have the first sub-suction surface approach or contact one end portion at the one end side of the main suction surface among a pair of mutually opposing end portions of the constituent element suctioned by the main suction surface of the suction pad, the second sub-suction surface approach or contact the other end portion at the other end side of the main suction surface, and the first sub-suction surface and the second sub-suction surface suction the end portions of the constituent element, and next, the first sub-suction surface and the second sub-suction surface move to the third position while still suctioning the constituent element and next, when the first sub-suction surface and the second sub-suction surface pass the third position, the constituent element suctioned by the first and second sub-suction surfaces is made to approach or contact the downstream conveying device and the constituent element is transferred to the downstream conveying device.

According to the above arrangement, the space between the first sub-suction surface and the second sub-suction surface when the first sub-suction surface and the second sub-suction surface pass the third position becomes greater than the space between the first sub-suction surface and the second sub-suction surface when the first sub-suction surface and the second sub-suction surface pass the second position and the constituent element is thereby transferred to the downstream conveying device in a state where a portion between the pair of end portions is stretched. Occurrence of wrinkles in the constituent element during the transfer can thereby be suppressed.

The space between the first sub-suction surface and the second sub-suction surface when the first sub-suction surface and the second sub-suction surface pass the third position is arranged to become greater than the space between the first sub-suction surface and the second sub-suction surface when the first sub-suction surface and the second sub-suction surface pass the second position, for example, by either or both of the first and second sub-suction pads that rotate around the second reference center line moving parallel to the second reference center line.

Preferably, the first virtual path surface and the second virtual path surface are cylindrical. The first reference center line and the second reference center line are parallel to each other. The first sub-suction pad rotates around a first rotational center line. The second sub-suction pad rotates around a second rotational center line. A portion of the first rotational center line further to the second sub-suction pad side than a first opposing portion opposing the first sub-suction pad and a portion of the second rotational center line further to the first sub-suction pad side than a second opposing portion opposing the second sub-suction pad intersect at an intersection and an angle at the second position side of angles formed by the first rotational center line and the second rotational center line is not less than 170° but less than 180°. A portion of the first rotational center line further to the first opposing portion side than the intersection and a portion of the second rotational center line further to the second opposing portion side than the intersection are positioned further to the second position side than a straight line that passes through the intersection and is parallel to the second reference center line.

In this case, the space between the first sub-suction surface and the second sub-suction surface when the first sub-suction surface and the second sub-suction surface pass the third position can be arranged to become greater than the space between the first sub-suction surface and the second sub-suction surface when the first sub-suction surface and the second sub-suction surface pass the second position by a simpler arrangement than in the case where either or both of the first and second sub-suction pads that rotate around the second reference center line moves or move parallel to the second reference center line.

Preferably, a controller is further included that is capable of making a first speed when the first sub-suction surface and the second sub-suction surface pass the second position and a second speed when the first sub-suction surface and the second sub-suction surface pass the third position differ.

In this case, a conveying pitch of constituent elements (distance in a conveying direction between mutually adjacent constituent elements) can be changed while conveying the constituent elements with the first sub-suction pad and the second sub-suction pad, thereby widening a range in which change in size can be accommodated.

In a preferable specific mode, the first sub-suction surface of the first sub-suction pad includes a first inner suction surface being a curved surface lying along a third virtual conical surface that is internally tangent to a first virtual conical surface contacting or approaching the first virtual path surface and being centered on the first rotational center line and is smaller in radius than the first virtual conical surface and a first outer suction surface being a portion of a cylindrical curved surface that is internally tangent to a first virtual cylindrical surface centered on the first rotational center line, the first virtual cylindrical surface being adjacent to a large diameter side of the first virtual conical surface, and is smaller in radius than the first virtual cylindrical surface. The second sub-suction surface of the second sub-suction pad includes a second inner suction surface being a curved surface lying along a fourth virtual conical surface that is internally tangent to a second virtual conical surface contacting or approaching the first virtual path surface and being centered on the second rotational center line, the second virtual conical surface being such that a small diameter side of the second virtual conical surface opposes a small diameter side of the first virtual conical surface, and is smaller in radius than the second virtual conical surface, and a second outer suction surface being a portion of a cylindrical curved surface that is internally tangent to a second virtual cylindrical surface centered on the second rotational centerline, the second virtual cylindrical surface being adjacent to a large diameter side of the second virtual conical surface, and is smaller in radius than the second virtual cylindrical surface.

In this case, at the second position, the first and second inner suction surfaces approach the main suction surface of the main suction pad more closely than the first and second outer suction surfaces, and at the third position, the first and second outer suction surfaces approach the downstream conveying device more closely than the first and second inner suction surfaces. The constituent element is transferred to the downstream conveying device in a state where the pair of end portions of the constituent element are suctioned to the first and second outer suction surfaces and the pair of end portions of the constituent element are stretched.

Also, to solve the above problem, the present invention provides a method for manufacturing absorptive article arranged as follows.

In a method for manufacturing absorptive article, a constituent element of an absorptive article is received from an upstream conveying device and after changing an orientation of the constituent element during conveying, it is transferred to a downstream conveying device. The method for manufacturing absorptive article includes (i) a first step in which a main suction surface that is curved to an arcuate surface shape between one end and another end and disengageably suctions the constituent element passes a first position and a second position by moving along a cylindrical or conical first virtual path surface centered on a first reference center line and in a circumferential direction of the first virtual path surface, the first virtual path surface being adjacent to the upstream conveying device at the first position, and while the main suction surface moves, a reference direction connecting the one end and the other end of the main suction surface changes in orientation with respect to the circumferential direction of the first virtual path surface, and when the main suction surface passes the first position, the main suction surface approaches or contacts the constituent element conveyed by the upstream conveying device and the main suction surface suctions the constituent element in a state where the reference direction and the circumferential direction of the first virtual path surface are parallel to each other, and next, while the main suction surface moves to the second position while still suctioning the constituent element, the orientation of the reference direction with respect to the circumferential direction of the first virtual path surface changes, and next, when the main suction surface passes the second position, the reference direction is made perpendicular to the circumferential direction of the first virtual path surface, and (ii) a second step in which a first sub-suction surface and a second sub-suction surface pass the second position and a third position at the same time as each other by moving, while being aligned with a space provided mutually therebetween, around a second reference center line and along a cylindrical or conical second virtual path surface centered on the second reference center line, the second virtual path surface being adjacent to the first virtual path surface at the second position and being adjacent to the downstream conveying device at the third position, and at the same time as when the main suction surface of the main suction pad passes the second position, the first sub-suction surface and the second sub-suction surface pass the second position, the first sub-suction surface approaches or contacts one end portion at the one end side of the main suction surface among a pair of mutually opposing end portions of the constituent element suctioned by the main suction surface of the main suction pad, the second sub-suction surface approaches or contacts the other end portion at the other end side of the main suction surface, and the first sub-suction surface and the second sub-suction surface suction the end portions of the constituent element, and next, the first sub-suction surface and the second sub-suction surface move to the third position while still suctioning the end portions of the constituent element and next, when the first sub-suction surface and the second sub-suction surface pass the third position, the constituent element the end portions of which are suctioned by the first sub-suction surface and second sub-suction surface is made to approach or contact the downstream conveying device and the constituent element is transferred to the downstream conveying device. In the second step, the space between the first sub-suction surface and the second sub-suction surface when the first sub-suction surface and the second sub-suction surface pass the third position is made greater than the space between the first sub-suction surface and the second sub-suction surface when the first sub-suction surface and the second sub-suction surface pass the second position.

According to the above method, the space between the first sub-suction surface and the second sub-suction surface when the first sub-suction surface and the second sub-suction surface pass the third position becomes greater than the space between the first sub-suction surface and the second sub-suction surface when the first sub-suction surface and the second sub-suction surface pass the second position and the constituent element is thereby transferred to the downstream conveying device in a state where a portion between the pair of end portions is stretched. Occurrence of wrinkles in the constituent element during the transfer can thereby be suppressed.

Preferably, the first virtual path surface and the second virtual path surface are cylindrical. The first reference center line and the second reference center line are parallel to each other. In the second step, (a) the first sub-suction pad rotates around a first rotational center line, (b) the second sub-suction pad rotates around a second rotational center line, (c) a portion of the first rotational center line further to the second sub-suction pad side than a first opposing portion opposing the first sub-suction pad and a portion of the second rotational center line further to the first sub-suction pad side than a second opposing portion opposing the second sub-suction pad intersect at an intersection and an angle at the second position side of angles formed by the first rotational center line and the second rotational center line is not less than 170° but less than 180°, and (d) a portion of the first rotational center line further to the first opposing portion side than the intersection and a portion of the second rotational center line further to the second opposing portion side than the intersection are positioned further to the second position side than a straight line that passes through the intersection and is parallel to the second reference center line.

In this case, the space between the first sub-suction surface and the second sub-suction surface when the first sub-suction surface and the second sub-suction surface pass the third position can be made greater than the space between the first sub-suction surface and the second sub-suction surface when the first sub-suction surface and the second sub-suction surface pass the second position more simply than in a case where either or both of the first and second sub-suction pads that rotate around the second reference center line moves or move parallel to the second reference center line.

Preferably, in the second step, a first speed when the first sub-suction surface and the second sub-suction surface pass the second position and a second speed when the first sub-suction surface and the second sub-suction surface pass the third position differ.

In this case, a conveying pitch of constituent elements (distance in a conveying direction between mutually adjacent constituent elements) can be changed while conveying the constituent elements with the first sub-suction pad and the second sub-suction pad, thereby widening a range in which change in size can be accommodated.

In a preferable specific mode, the first sub-suction surface of the first sub-suction pad includes a first inner suction surface being a curved surface lying along a third virtual conical surface that is internally tangent to a first virtual conical surface contacting or approaching the first virtual path surface and being centered on the first rotational center line and is smaller in radius than the first virtual conical surface and a first outer suction surface being a portion of a cylindrical curved surface that is internally tangent to a first virtual cylindrical surface centered on the first rotational center line, the first virtual cylindrical surface being adjacent to a large diameter side of the first virtual conical surface, and is smaller in radius than the first virtual cylindrical surface. The second sub-suction surface of the second sub-suction pad includes a second inner suction surface being a curved surface lying along a fourth virtual conical surface that is internally tangent to a second virtual conical surface contacting or approaching the first virtual path surface and being centered on the second rotational center line, the second virtual conical surface being such that a small diameter side of the second virtual conical surface opposes a small diameter side of the first virtual conical surface, and is smaller in radius than the second virtual conical surface, and a second outer suction surface being a portion of a cylindrical curved surface that is internally tangent to a second virtual cylindrical surface centered on the second rotational centerline, the second virtual cylindrical surface being adjacent to a large diameter side of the second virtual conical surface, and is smaller in radius than the second virtual cylindrical surface.

In this case, at the second position, the first and second inner suction surfaces approach the main suction surface of the main suction pad more closely than the first and second outer suction surfaces, and at the third position, the first and second outer suction surfaces approach the downstream conveying device more closely than the first and second inner suction surfaces. The constituent element is transferred to the downstream conveying device in a state where the pair of end portions of the constituent element are suctioned to the first and second outer suction surfaces and the pair of end portions of the constituent element are stretched.

Advantageous Effects of Invention

By the present invention, occurrence of wrinkles in a constituent element of an absorptive article when the constituent element is transferred to a downstream conveying device can be suppressed.

BRIEF DESCRIPTION OF DRAWINGS

FIG. 4(a) is a front view of sub-suction pads.

FIG. 4(b) is a development view of the sub-suction pads. (Example 1)

DESCRIPTION OF EMBODIMENTS

Embodiments of the present invention shall now be described with reference to the drawings.

Example 1

An apparatus 10 for manufacturing and a method for manufacturing absorptive article of Example 1 shall be described with reference to FIG. 1 to FIG. 6.

Figure 1:
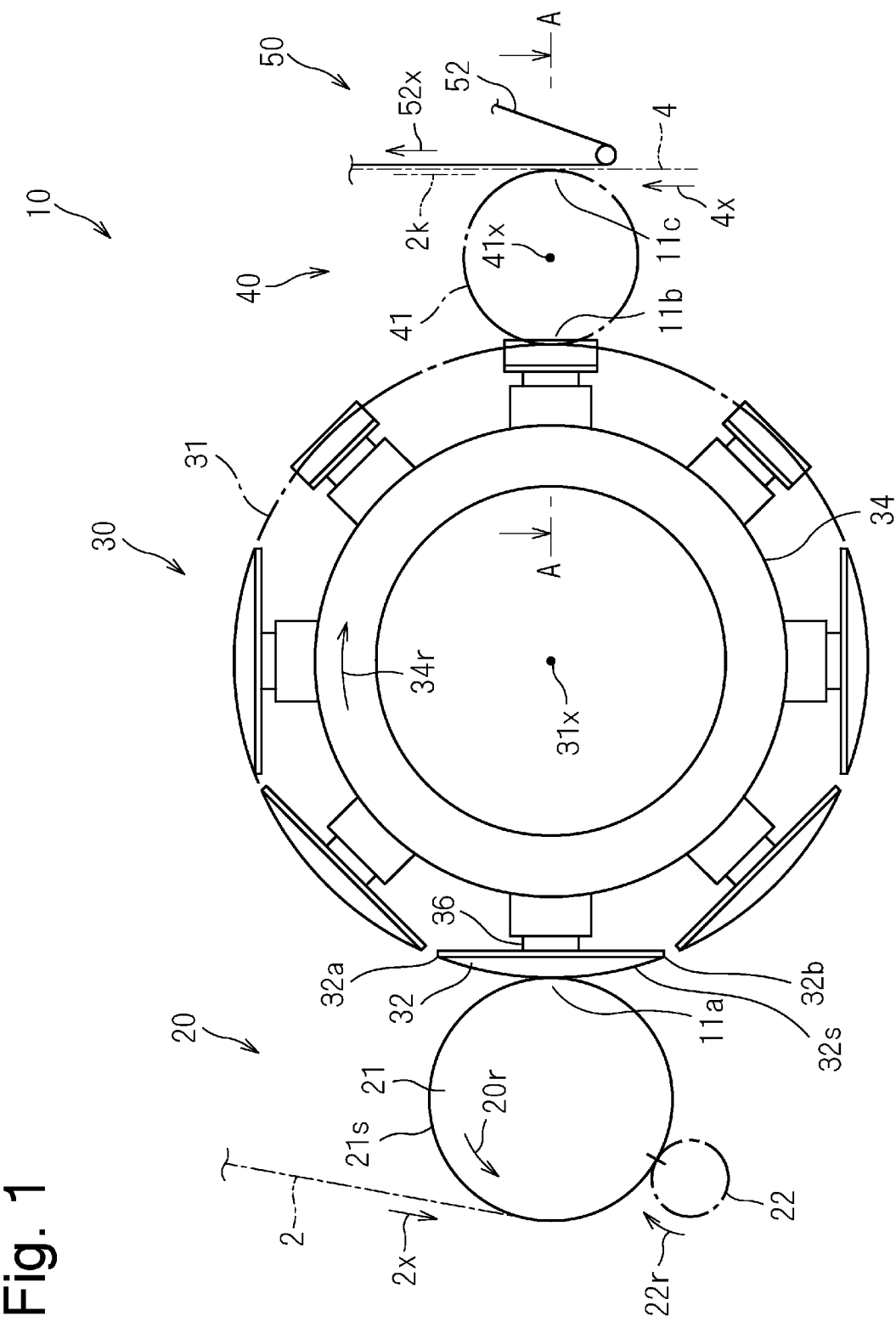
FIG. 1 is a schematic diagram showing an overall arrangement of an apparatus for manufacturing absorptive article. (Example 1)

FIG. 1 is a schematic diagram showing an overall arrangement of the apparatus 10 for manufacturing absorptive article. As shown in FIG. 1, the apparatus 10 for manufacturing absorptive article has a first device 30 and a second device 40 disposed between an upstream conveying device 20 and a downstream conveying device 50. The upstream conveying device 20 and the first device 30 are mutually adjacent at a first position 11a. The first device 30 and the second device 40 are mutually adjacent at a second position 11b. The second device 40 and the downstream conveying device 50 are mutually adjacent at a third position 11c.

The upstream conveying device 20 suctions a first continuous body 2 conveyed in a direction indicated by an arrow 2x onto an outer circumferential surface 21s of a rotating drum 21 rotating in a direction indicated by an arrow 20r. The first continuous body 2 is cut at predetermined intervals and divided into individual pieces of constituent elements 2k when passing through a cutting mechanism 22 in which a cutter blade rotates in a direction indicated by an arrow 22r.

The first device 30 receives each constituent element 2k from the upstream conveying device 20 and after changing an orientation of the constituent element 2k, transfers it to the second device 40. The second device 40 transfers the constituent element 2k to the downstream conveying device 50.

The downstream conveying device 50 has a conveyor belt 52 moving in a direction indicated by an arrow 52x and conveys a second continuous body 4 in a direction indicated by an arrow 4x. The downstream conveying device 50 conveys the constituent element 2k along with the second continuous body 4 in a state where the constituent element 2k received from the second device 40 is superposed on the second continuous body 4.

Figure 6:
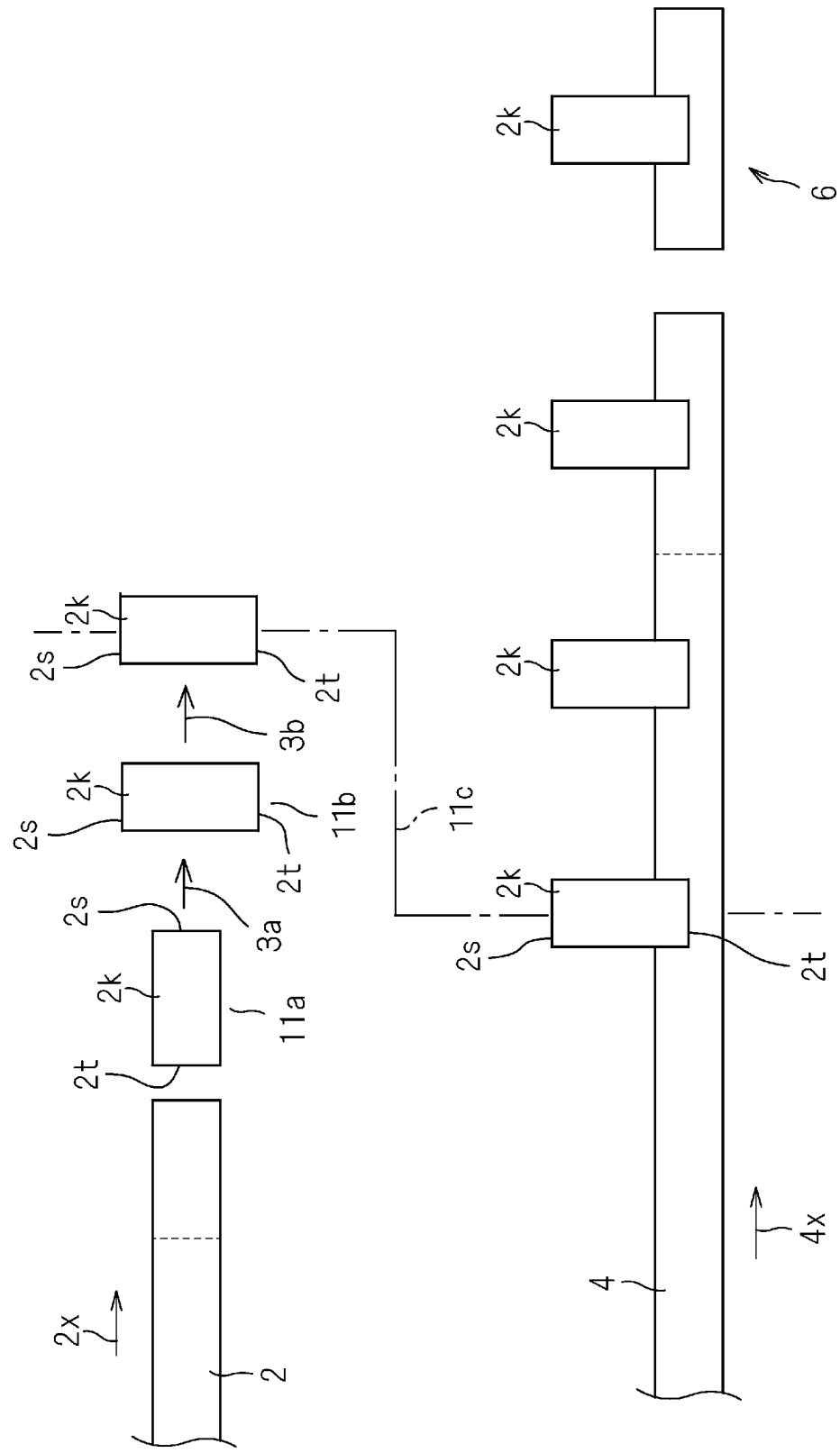
FIG. 6 is a schematic view showing an outline of a manufacturing process for an absorptive article. (Example 1)

FIG. 6 is a schematic view showing an outline of a manufacturing process for an absorptive article 6. As shown in FIG. 6, the first continuous body 2 is conveyed in the direction indicated by the arrow 2x and is divided into the individual pieces of the constituent elements 2k while being conveyed. The first device 30 (see FIG. 1) receives each constituent element 2k from the upstream device 20 (see FIG. 1) at the first position 11a and while conveying the constituent element 2k to the second position 11b, changes the orientation of the constituent element 2k by 90° with respect to a conveying direction of the constituent element 2k indicated by an arrow 3a. That is, a direction connecting one end 2s and another end 2t at which the constituent element 2k was cut becomes perpendicular to the conveying direction 3a of the constituent element 2k. Next, the second device 40 (see FIG. 1) receives the constituent element 2k from the first device 30 (see FIG. 1) at the second position 11b, conveys the constituent element 2k while maintaining the orientation of the constituent element 2k with respect to a conveying direction of the constituent element 2k indicated by an arrow 3b, and transfers the constituent element 2k to the downstream conveying device 50 (see FIG. 1) at the third position 11c. The constituent element 2k is superposed on the second continuous body 4 being conveyed in the direction indicated by the arrow 4x and after being conveyed integrally with the second continuous body 4, the second continuous body 4 is cut between mutually adjacent constituent elements 2k and divided into individual pieces of the absorptive articles 6.

For example, the absorptive article 6 is a disposable paper diaper and the constituent element 2k is an absorptive main body that includes a top sheet, a back sheet, and an absorptive core. The constituent elements 2k are disposed at predetermined intervals, that is, intermittently on the second continuous body 4 that is a continuous web of a waist member.

Next, the first device 30 of the apparatus 10 for manufacturing absorptive article shall be described. As shown in FIG. 1, with the first device 30, support shafts 36 extending in radial directions of a rotating drum 34 are rotatably supported on the rotating drum 34 that rotates in a direction of an arrow 34r and a main suction pad 32 is fixed on an end portion at a radially outer side of each support shaft 36. An unillustrated cam follower that engages with unillustrated cam is fixed to an end portion at a radially inner side of the support shaft 36 and the support shaft 36 is arranged such that it rotates forward and in reverse in a range of 90° and the main suction pad 32 rocks and changes in orientation by 90° around the support shaft 36 when the rotating drum 34 rotates.

Figure 2:
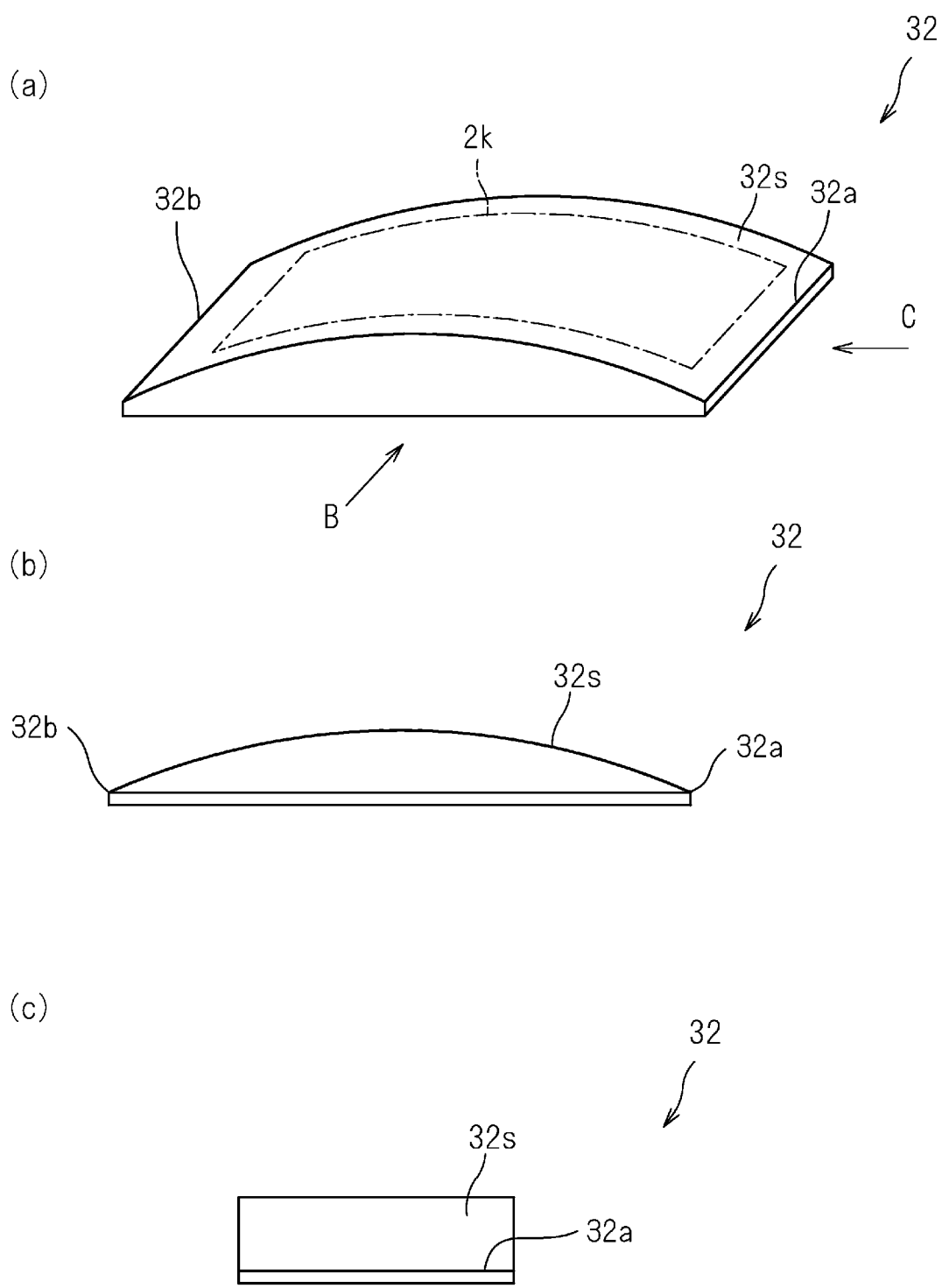
FIG. 2(a) is a perspective view showing a general arrangement of a main suction pad.
FIG. 2(b) is a front view of the main suction pad.
FIG. 2(c) is a side view of the main suction pad. (Example 1)

FIG. 2(a) is a perspective view showing a general arrangement of the main suction pad 32. FIG. 2 (b) is a front view as viewed from a direction indicated by an arrow B in FIG. 2(a). FIG. 2(c) is a side view as viewed from a direction indicated by an arrow C in FIG. 2(a). As shown in FIG. 1 and FIG. 2, the main suction pad 32 has a main suction surface 32s curved to an arcuate surface shape between one end 32a and another end 32b. Although not illustrated, unillustrated suction holes in communication with a negative pressure source are formed in the main suction pad 32 and the suction holes open to the main suction surface 32s. The constituent element 2k can thereby be suctioned onto the main suction surface 32s.

As shown in FIG. 1, the main suction surface 32s moves along a cylindrical first virtual path surface 31 centered on a first reference center line 31x and moves in a circumferential direction of the first virtual path surface 31. The first virtual path surface 31 is adjacent to the upstream conveying device 20 at the first position 11a and adjacent to the second device 40 at the second position 11b.

During movement, the main suction pad 32 changes in orientation with respect to a movement direction, that is, in orientation of a reference direction connecting one end 32a and another end 32b of the main suction surface 32s with respect to the circumferential direction of the first virtual path surface 31. This reference direction is parallel to the circumferential direction of the first virtual path surface 31 when the main suction surface 32s passes the first position 11a and is perpendicular to the circumferential direction of the first virtual path surface 31 when the main suction surface 32s passes the second position 11b.

The main suction surface 32s is formed such that when passing the first position 11a, it is coincident or substantially coincident with an arcuate surface constituting a portion of a cylindrical surface that is internally tangent to the first virtual path surface 31, is centered on an axis parallel to the first reference center line 31x, and is of a slightly smaller radius than a radius of the first virtual path surface 31.

Next, the second device 40 shall be described. As shown in FIG. 1, with the second device 40, first and second sub-suction pads to be described below move around a second reference center line 41x and along a cylindrical second virtual path surface 41 centered on the second reference center line 41x. The second virtual path surface 41 is adjacent to the first virtual path surface 31 at the second position 11b and is adjacent to the downstream conveying device 50 at the third position 11c.

Figure 3:
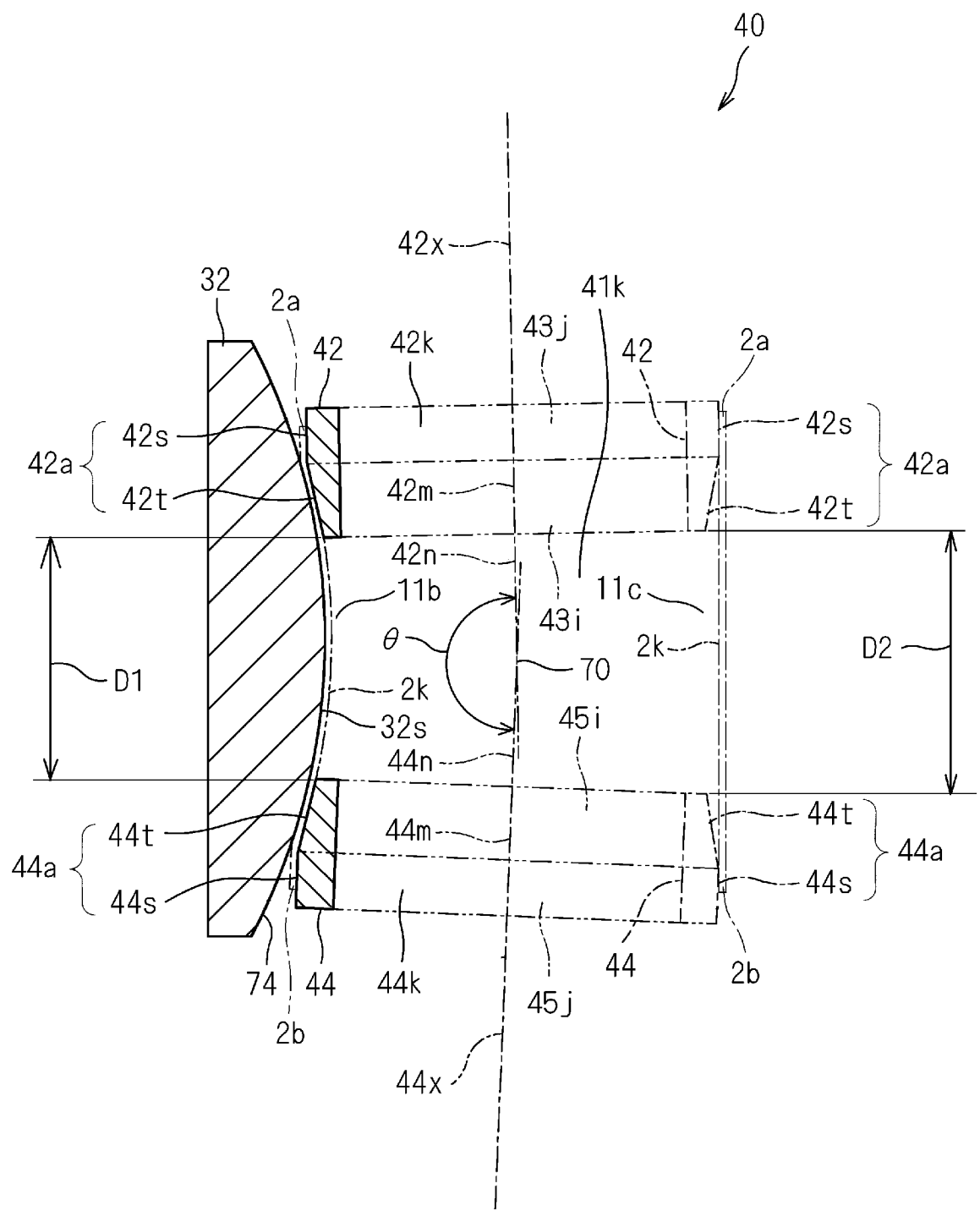
FIG. 3 is a schematic view of a cross section taken along line A-A of FIG. 1. (Example 1)

FIG. 3 is a schematic view of a cross section taken along line A-A of FIG. 1. As shown in FIG. 3, with the second device 40, the first sub-suction pad 42 rotates around a first rotational center line 42x and the second sub-suction pad 44 rotates around a second rotational center line 44x. The first sub-suction pad 42 has a first sub-suction surface 42a. The second sub-suction pad 44 has a second sub-suction surface 44a. The first and second sub-suction pads 42 and 44 move along the second virtual path surface 41 and around the second reference center line 41x shown in FIG. 1 while being aligned with a space being provided between the first sub-suction surface 42a and the second sub-suction surface 44a.

As indicated by solid lines in FIG. 3, with the first and second sub-suction pads 42 and 44, the first and second sub-suction surfaces 42a and 44a pass the second position 11b at the same time. At this point, the first and second sub-suction surfaces 42a and 44a approach or contact a pair of mutually opposing end portions 2a and 2b of the constituent element 2k suctioned on the main suction surface 32s of the main suction pad 32. While suctioning the end portions 2a and 2b of the constituent element 2k on the first and second sub-suction surfaces 42a and 44a, the first and second sub-suction pads 42 and 44 rotate and move to the third position 11c as indicated by dot-dash lines.

At least one of either of the first and second rotational center lines 42x and 44x extends in a direction slightly inclined from a direction parallel to the second reference center line 41x (see FIG. 1). The first and second rotational center lines 42x and 44x intersect each other in a third region 41k between a first region 42k in which the first sub-suction pad 42 moves and a second region 44k in which the second sub-suction pad 44 moves. An angle θ at the second position 11b side formed by the first rotational center line 42x and the second rotational center line 44x is slightly smaller than 180°. Therefore, with the first and second sub-suction pads 42 and 44, a space D2 between the first sub-suction surface 42a and the second sub-suction surface 44a when the first and second sub-suction surfaces 42a and 44a pass the third position 11c becomes greater than a space D1 between the first sub-suction surface 42a and the second sub-suction surface 44a when the first and second sub-suction surfaces 42a and 44a pass the second position 11b. Thereby, the constituent element 2k with which the end portions 2a and 2b are suctioned onto the first and second sub-suction surfaces 42a and 44a at the second position 11b becomes stretched in a portion between the pair of end portions 2a and 2b at the third position 11c.

In detail, a portion 42n of the first rotational center line 42x further to the second sub-suction pad 44 side than a first opposing portion 42m opposing the first sub-suction pad 42 and a portion 44n of the second rotational center line 44x further to the first sub-suction pad 42 side than a second opposing portion 44m opposing the second sub-suction pad 44 intersect at an intersection 70, and the angle θ at the second position 11b side of angles formed by the first rotational center line 42x and the second rotational center line 44x is not less than 170° but less than 180°. Also, a portion of the first rotational center line 42x further to the first opposing portion 42m side than the intersection 70 and a portion of the second rotational center line 44x further to the second opposing portion 44m side than the intersection 70 are positioned further to the second position 11b side than a straight line that passes through the intersection 70 and is parallel to the second reference center line 41x (see FIG. 1).

The first and second sub-suction pads 42 and 44 may be the same or different in dimensions and shape. FIG. 4(a) is a front view of the first and second sub-suction pads 42 and 44 as viewed from a direction parallel to the first and second rotational center lines 42x and 44x. FIG. 4(b) is a development view of the first and second sub-suction surfaces 42a and 44a of the first and second sub-suction pads 42 and 44.

As shown in FIG. 3 and FIG. 4, the first sub-suction surface 42a of the first sub-suction pad 42 includes a first inner suction surface 42t and a first outer suction surface 42s. The second sub-suction surface 44a of the second sub-suction pad 44 includes a second inner suction surface 44t and a second outer suction surface 44s. The first inner suction surface 42t lies along a third virtual conical surface that is internally tangent to a first virtual conical surface 43i centered on the first rotational center line 42x and is smaller in radius than the first virtual conical surface 43i. The first outer suction surface 42s is a portion of a cylindrical curved surface that is internally tangent to a first virtual cylindrical surface 43j centered on the first rotational center line 42x, the first virtual cylindrical surface 43j being adjacent to a large diameter side of the first virtual conical surface 43i, and is smaller in radius than the first virtual cylindrical surface 43j. The second inner suction surface 44t lies along a fourth virtual conical surface that is internally tangent to a second virtual conical surface 45i centered on the second rotational center line 44x and is smaller in radius than the second virtual conical surface 43i. A small diameter side of the second virtual conical surface 45i and a small diameter side of the first virtual conical surface 43i oppose each other. The second outer suction surface 44s is a portion of a cylindrical curved surface that is internally tangent to a second virtual cylindrical surface 45j centered on the second rotational center line 44x, the second virtual cylindrical surface 45j being adjacent to a large diameter side of the second virtual conical surface 45i, and is smaller in radius than the second virtual cylindrical surface 45j. The first and second virtual conical surfaces 43i and 45i approach or contact the first virtual path surface 31 along which the main suction pad 32 moves.

Figure 5:
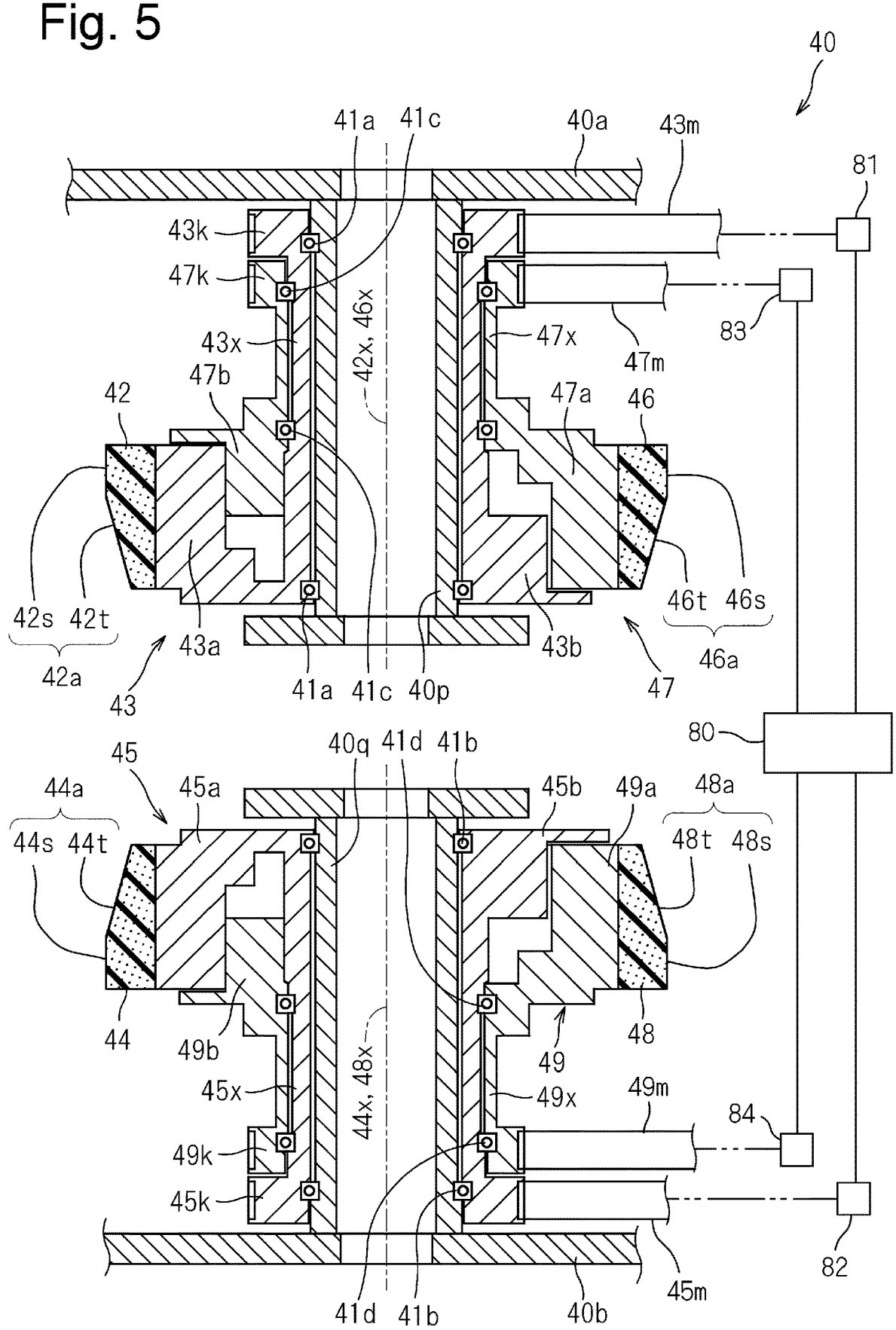
FIG. 5 is a sectional view of principal portions of a second device. (Example 1)

As shown in FIG. 3 to FIG. 5, intersection lines of the inner suction surfaces 42t and 44t; 46t and 48t of the sub-suction surfaces 42a and 44a; 46a and 48a with a plane containing the rotational center lines 42x and 44x; 46x and 48x are straight lines and lie along the main suction surface 32 at the second position 11b.

As shown in FIG. 3, at the second position 11b, the first and second inner suction surfaces 42t and 44t approach the main suction surface 32s of the main suction pad 32 more closely than the first and second outer suction surfaces 42s and 44s. At the third position 11c, the first and second outer suction surfaces 42s and 44s approach the downstream conveyer device 50 more closely than the first and second inner suction surfaces 42t and 44t. The constituent element 2k is transferred to the downstream conveyer device 50 in a state where the end portions 2a and 2b of the constituent element 2k are suctioned onto the first and second outer suction surfaces 42s and 44s and the portion between the end portions 2a and 2b of the constituent element 2k is stretched.

As shown in FIG. 4, suction holes 42p and 44p in communication with a negative pressure source are formed in the first and second sub-suction pads 42 and 44, and openings 42q and 44q of the suction holes 42p and 44p are formed in the first and second sub-suction surfaces 42a and 44a. The first and second sub-suction pads 42 and 44 can thereby suction the constituent element 2k. Dimensions, shapes, configuration, etc., of the suction holes 42p and 44p and the openings 42q and 44q should be selected as appropriate. For the first and second sub-suction pads 42 and 44, an elastic member of rubber, etc., is preferably used and, for example, silicon rubber is used.

FIG. 5 is a sectional view of principal portions of the second device 40. As shown in FIG. 5, a first set of the first and second sub-suction pads 42 and 44 and a second set of first and second sub-suction pads 46 and 48 are disposed coaxially and are arranged to rotate deviatedly with respect to each other in a circumferential direction. Just one set of the first and second sub-suction pads may be provided or three or more sets may be provided.

The first sub-suction pad 46 of the second set is the same in arrangement as the first sub-suction pad 42 of the first set, and the first sub-suction surface 46a of the first sub-suction pad 46 of the second set includes a first inner suction surface 46t and a first outer suction surface 46s. The second sub-suction pad 48 of the second set is the same in arrangement as the second sub-suction pad 44 of the first set, and the second sub-suction surface 48a of the second sub-suction pad 48 of the second set includes a second inner suction surface 48t and a second outer suction surface 48s.

The sub-suction pads 42, 44, 46, and 48 are respectively fixed to pad supporting portions 43a, 45a, 47a, and 49a of rotating members 43, 45, 47, and 49 that rotate around rotational center lines 42x, 44x, 46x, and 48x. The first rotational center line 42x of the first rotating member 43 of the first set is coincident with the first rotational center line 46x of the first rotating member 47 of the second set. The second rotational center line 44x of the second rotating member 45 of the first set is coincident with the second rotational center line 48x of the second rotating member 49 of the second set. The rotating members 43, 45, 47, and 49 respectively have the pad supporting portions 43a, 45a, 47a, and 49a and balancing weight portions 43b, 45b, 47b, and 49b fixed to one end sides of shaft portions 43x, 45x, 47x, and 49x and have pulleys 43k, 45k, 47k and 49k fixed to other end sides of the shaft portions 43x, 45x, 47x, and 49x.

The shaft portions 43x and 45x of the first and second rotating members 43 and 45 of the first set are rotatably supported via bearings 41a and 41b on support shafts 40p and 40q fixed to base frames 40a and 40b. The shaft portions 45x and 47x of the first and second rotating members 47 and 49 of the second set are rotatably supported via bearings 41c and 41d on outer peripheries of the shaft portions 43x and 45x of the first and second rotating members 43 and 45 of the first set. The pad supporting portions 43a, 45a, 47a, and 49a and the balancing weight portions 43b, 45b, 47b, and 49b are disposed substantially opposingly across the shaft portions 43x, 45x, 47x, and 49x. Rotations are transmitted to the pulleys 43k, 45k, 47k and 49k respectively from servo motors 81, 82, 83, and 84 via timing belts 43m, 45m, 47m, and 49m. The rotations of the servo motors 81, 82, 83, and 84 are controlled by a controller 80.

The controller 80 can make moving speed of the first and second sub-suction pads 42 and 44; 46 and 48 differ at the second position 11b and the third position 11c by controlling the rotations of the servo motors 81, 82, 83, and 84. In this case, a conveying pitch of the constituent elements 2k, that is, a distance in a conveying direction between mutually adjacent constituent elements 2k can be changed while a constituent element 2k passes the second device 40.

A separating step of changing the conveying pitch at the second device 40 is thereby added. A range in which change in size can be accommodated is thus widened.

Next, operation of the apparatus 10 for manufacturing absorptive article shall be described.

The main suction pad 32 of the first device 30, with the main suction surface 32s approaching or contacting the constituent element 2k conveyed by the upstream conveying device 20 at the first position 11a, suctions the constituent element 2k onto the main suction surface 32s and thereafter moves to the second position 11b with the constituent element 2k still being suctioned on the main suction surface 32s. At the same time as when the main suction surface 32s of the main suction pad 32 passes the second position 11b, the first and second sub-suction surfaces 42a and 44a (or 46a and 48a) of the first and second sub-suction pads 42 and 44 (or 46 and 48) pass the second position 11b. At this point, the first and second sub-suction pads 42 and 44 (or 46 and 48) of the second device 40 have the first sub-suction surface 42a (or 46a) approach or contact the one end portion 2a among the pair of mutually opposing end portions 2a and 2b of the constituent element 2k suctioned by the main suction surface 32s of the main suction pad 32 and the second sub-suction surface 44a (or 48a) approach or contact the other end portion 2b and suction the end portions 2a and 2b of the constituent element 2k onto the first and second sub-suction surfaces 42a and 44a (or 46a and 48a), and next, the first and second sub-suction surfaces 42a and 44a (or 42a and 48a) move to the third position 11c while still suctioning the constituent element 2k and next, at the third position 11c, the constituent element 2k suctioned by the first and second sub-suction surfaces 42a and 44a (or 46a and 48a) is made to approach or contact the downstream conveying device 50 and the constituent element 2k is transferred to the downstream conveying device 50.

The space D2 between the first sub-suction surface 42a (or 46a) and the second sub-suction surface 44a (or 48a) at the third position 11c becomes greater than the space D1 between the first sub-suction surface 42a (or 46a) and the second sub-suction surface 44a (or 48a) at the second position 11b and the constituent element 2k is thereby transferred to the downstream conveying device 50 in the state where the portion between the end portions 2a and 2b of the constituent element 2k is stretched. Occurrence of wrinkles in the constituent element 2k when being transferred to the downstream conveying device 50 can thereby be suppressed.

Even when an elastic member of rubber, etc., is disposed in the constituent element 2k such as to extend in the direction connecting the one end portion 2a and the other end portion 2b of the constituent element 2k, the occurrence of wrinkles can be suppressed by suctioning the end portions 2a and 2b of the constituent element 2k and stretching the portion between the end portions 2a and 2b.

Next, a method for manufacturing absorptive article using the apparatus 10 for manufacturing absorptive article shall be described.

(1) First, the main suction surface 32s that is curved to the arcuate surface shape between the one end 32a and the other end 32b and disengageably suctions the constituent element 2k passes the first position 11a and the second position 11b by moving along the cylindrical first virtual path surface 31 centered on the first reference center line 31x and in the circumferential direction of the first virtual path surface 31, the first virtual path surface 31 being adjacent to the upstream conveying device 20 at the first position 11a, and while the main suction surface 32s moves, the reference direction connecting the one end 32a and the other end 32b of the main suction surface 32s changes in orientation with respect to the circumferential direction of the first virtual path surface 31 and (a) when the main suction surface 32s passes the first position 11a, the main suction surface 32s approaches or contacts the constituent element 2k conveyed by the upstream conveying device 20 and the main suction surface 32s suctions the constituent element 2k in the state where the reference direction and the circumferential direction of the first virtual path surface 31 are parallel to each other, and (b) next, while the main suction surface 32s moves to the second position 11b while still suctioning the constituent element 2k, the orientation of the reference direction with respect to the circumferential direction of the first virtual path surface 31 changes, and (c) next, when the main suction surface 32s passes the second position 11b, the reference direction is made perpendicular to the circumferential direction of the first virtual path surface 31. The above is a first step.

(2) The first sub-suction surface 42a; 46a and the second sub-suction surface 44a; 48a pass the second position 11b and the third position 11c at the same time as each other by moving, while being aligned with a space provided mutually therebetween, around the second reference center line 41x and along the cylindrical second virtual path surface 41 centered on the second reference center line 41x, the second virtual path surface 41 being adjacent to the first virtual path surface 31 at the second position 11b and being adjacent to the downstream conveying device 50 at the third position 11c, and (a) at the same time as when the main suction surface 32s of the main suction pad 32 passes the second position 11b, the first sub-suction surface 42a; 46a and the second sub-suction surface 44a; 48a pass the second position 11b, the first sub-suction surface 42a; 46a approaches or contacts the one end portion 2a among the pair of mutually opposing end portions 2a and 2b of the constituent element 2k suctioned by the main suction surface 32s of the main suction pad 32, the second sub-suction surface 44a; 48a approaches or contacts the other end portion 2b, and the first sub-suction surface 42a; 46a and the second sub-suction surface 44a; 48a suction the end portions 2a and 2b of the constituent element 2k, and (b) next, the first sub-suction surface 42a; 46a and the second sub-suction surface 44a; 48a move to the third position 11c while still suctioning the end portions 2a and 2b of the constituent element 2k and (c) next, when the first sub-suction surface 42a; 46a and the second sub-suction surface 44a; 48a pass the third position 11c, the constituent element 2k the end portions 2a and 2b of which are suctioned by the first sub-suction surface 42a; 46a and the second sub-suction surface 44a; 48a is made to approach or contact the downstream conveying device 50 and the constituent element 2k is transferred to the downstream conveying device 50 (see FIG. 1). The space D2 between the first sub-suction surface 42a; 46a and the second sub-suction surface 44a; 48a when the first sub-suction surface 42a; 46a and the second sub-suction surface 44a; 48a pass the third position 11c is made greater than the space D1 between the first sub-suction surface 42a; 44a and the second sub-suction surface 44a; 48a when the first sub-suction surface 42a; 44a and the second sub-suction surface 44a; 48a pass the second position 11b. The above is the second step.

By the above method, the constituent element 2k of the absorptive article can be received from the upstream conveying device 20 and after changing the orientation of the constituent element 2k during conveying, it can be transferred to the downstream conveying device 50. The constituent element 2k is transferred to the downstream conveying device 50 in the stretched state and therefore, the occurrence of wrinkles in the constituent element 2k when transferring the constituent element 2k to the downstream conveying device 50 can be suppressed.

Modification Example 1

The space between the first sub-suction surface and the second sub-suction surface when the first sub-suction surface and the second sub-suction surface pass the third position is arranged to become greater than the space between the first sub-suction surface and the second sub-suction surface when the first sub-suction surface and the second sub-suction surface pass the second position by either or both of the first and second sub-suction pads that rotate around the second reference center line moving parallel to the second reference center line. In this case, either or both of the first and second sub-suction pads move or moves parallel to the second reference center line and therefore, the arrangement becomes more complex in comparison to the apparatus 10 for manufacturing absorptive article of Example 1.

Example 2

An apparatus for manufacturing absorptive article of Example 2 shall be described with reference to FIG. 8 and FIG. 9. In the following, arrangements of a main suction pad and sub-suction pads that are the points of difference with respect to the apparatus 10 for manufacturing absorptive article of Example 1 shall mainly be described.

Figure 7:
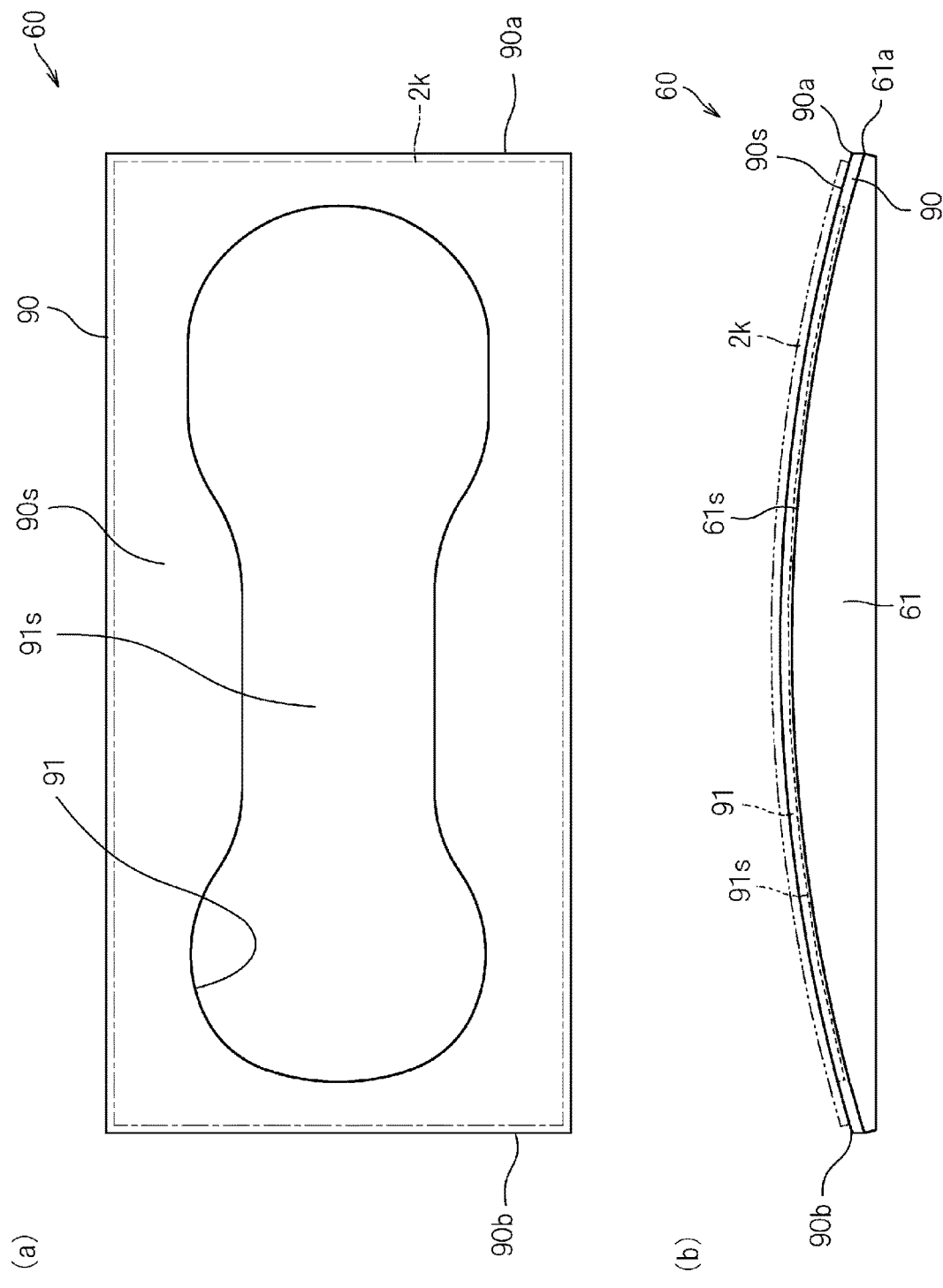
FIG. 7(a) is a plan view of a main suction pad and FIG. 7(b) is a side view of the main suction pad. (Example 2)

First, a first device of the apparatus for manufacturing absorptive article shall be described. FIG. 7(a) is a plan view of a main suction pad 60 that the first device has and FIG. 7(b) is a side view of the main suction pad 60. As shown in FIGS. 7(a) and 7(b), an elastic sheet 90 of constant thickness is attached to a curved surface 61s curved to an arcuate surface shape from one end 61a to another end 61b of a main body 61 of the main suction pad 60. The elastic sheet 90 has a recess 91 formed in an inner region of one main surface 90s at a side opposite to the main body 61. Although not illustrated, suction holes in communication with a negative pressure source are formed in the main body 61 and the elastic sheet 90 and the suction holes open to the one main surface 90s and a bottom surface 91s of the recess 91 of the elastic sheet 90. The one main surface 90s and the bottom surface 91s of the recess 91 of the elastic sheet 90 are main suction surfaces 90s and 91s that are curved to arcuate surface shapes from one end 90a to another end 90b and disengageably suction the constituent element 2k. As in Example 1, the main suction pad 60 moves along a cylindrical first virtual path surface, receives the constituent element 2k from an upstream conveying device at a first position, conveys the constituent element 2k while holding it, and transfers the constituent element 2k to a second device at a second position.

If the constituent element 2k suctioned and conveyed by the main suction pad 60 is, for example, an absorptive main body having an absorptive core disposed between a top sheet and a back sheet, the constituent element 2k is greater in thickness at an inner region that is surrounded by a peripheral region and in which the absorptive core is disposed between the two sheets than at the peripheral region in which the two sheets are bonded to each other. The elastic sheet 90 is arranged such that when suctioning and holding such a constituent element 2k that differs in thickness, the inner region of large thickness of the constituent element 2k is suctioned and held by the bottom surface 91s of the recess 91 of the elastic sheet 80 and the peripheral region of small thickness of the constituent element 2k is suctioned and held by the one main surface 90s of the elastic sheet 90. The recess 91 is arranged such that when holding the inner region of large thickness of the constituent element 2k, the inner region of the constituent element 2k does not project radially outward excessively.

By providing the main body 61 of the main suction pad 60 with the elastic sheet 90 with the recess 91 formed therein, the main suction pad 60 is made capable of more readily receiving the constituent element 2k from the upstream device 20 and more readily holding the constituent element 2k than the main suction pad 32 of Example 1.

By providing the main body 61 of the main suction pad 60 with the elastic sheet 90, the occurrence of wrinkles in the constituent element 2k and biting-in of the constituent element 2k can be prevented even when the main suction pad 60 is pressed against and put in close contact with the constituent element 2k held by the upstream conveying device 20 (see FIG. 1) when receiving the constituent element 2k from the upstream conveying device 20 (see FIG. 1). Transfer of the constituent element 2k from the upstream conveying device 20 (see FIG. 1) to the main suction pad 60 is thus stabilized further.

Next, the second device of the apparatus for manufacturing absorptive article shall be described. As with FIG. 3, FIG. 8 is a sectional view of principal portions of the second device. FIG. 9 is an enlarged sectional view of principal portions enlarging a portion of FIG. 8. As shown in FIG. 8 and FIG. 9, the second device, as in Example 1, has a first set of first and second sub-suction pads 62 and 64 and a second set of first and second sub-suction pads 66 and 68. The sub-suction pads 62 and 64; 66 and 68 move along the cylindrical second virtual path surface 41 (see FIG. 1) and pass the second and third positions 11b and 11c. The first sub-suction pad 62; 66 rotates around a first rotational center line 63 and the second sub-suction pad 64; 68 rotates around a second rotational center line 65. The space D2 between the first and second sub-suction pads 62 and 64; 66 and 68 when passing the third position 11c is arranged to become greater than the space D1 between the first and second sub-suction pads 62 and 64; 66 and 68 when passing the second position 11b. The respective sub-suction pads 62 and 64; 66 and 68 are the same in dimensions and shape.

Unlike in Example 1, each of the sub-suction pads 62 and 64; 66 and 68 has a main body 98 having stepped shape and three first to third elastic sheets 92, 94, and 96 attached to the main body 98. Each of the first to third elastic sheets 92, 94, and 96 is of constant thickness. As shown in FIG. 9, the main body 98 has first to third curved surfaces 98a, 98b, and 98c that are formed with steps such that angles with respect to the rotational center lines 63 and 65 increase toward an outer side in directions parallel to the rotational center lines 63 and 65, that is, with separation from a center line 67 between the first sub-suction pads 62 and 66 and the second sub-suction pads 64 and 68 and a fourth curved surface 98*d* that is continuous to the curved surface 98*c* at the outer side and with which distances from the rotational center lines 63 and 65 are constant in the directions parallel to the rotational center lines 63 and 65.

The third elastic sheet 96 is disposed such as to contact the third and fourth curved surfaces 98*c* and 98*d*. The second elastic sheet 94 is disposed such as to contact the third elastic sheet 96 and the second curved surface 98*b*. The first elastic sheet 92 is disposed such as to contact the second elastic sheet 94 and the first curved surface 98*a*.

First sub-suction surfaces 62*a* and 66*a* of the first sub-suction pads 62 and 66 are surfaces of the first elastic sheets 92 at sides opposite to the main bodies 98. The first sub-suction surfaces 62*a* and 66*a* include first inner suction surfaces 62*t* and 66*t* and first outer suction surfaces 62*s* and 66*s*. Main surfaces 64*a* and 68*a* of the first elastic sheets 92 of the second sub-suction pads 64 and 68 at sides opposite to the main bodies 98 are second sub-suction surfaces 64*a* and 64*a*. The second sub-suction surfaces 64*a* and 68*a* include second inner suction surfaces 64*t* and 68*t* and second outer suction surfaces 64*s* and 68*s*.

The inner suction surfaces 62*t* and 64*t*; 66*t* and 68*t* are portions opposing the first to third curved surfaces 98*a*, 98*b*, and 98*c* of the main bodies 98 and oppose the main suction surfaces 90*s* and 91*s* of the main suction pad 60 at the second position 11*b* and move along truncated conical paths 69*t* centered on the rotational center lines 63 and 65. The outer suction surfaces 62*s* and 64*s*; 66*s* and 68*s* are portions opposing the fourth curved surfaces 98*d* of the main bodies 98 and oppose the main suction surface 90*s* of the main suction pad 60 with wedge-shaped spaces 99 provided in between at the second position 11*b* and move along cylindrical paths 69*s* centered on the rotational center lines 63 and 65.

The first inner suction surfaces 62*t* and 66*t* are curved surfaces lying along a third virtual conical surface 43*i* (see FIG. 3 and FIG. 4) at a radially outer side of the third virtual conical surface that is internally tangent to a first virtual conical surface 43*i* (see FIG. 3 and FIG. 4) centered on the first rotational center line 63 and is smaller in radius than the first virtual conical surface. The second inner suction surfaces 64*t* and 68*t* are curved surfaces lying along a fourth virtual conical surface at an outer side of the fourth virtual conical surface that is internally tangent to a second virtual conical surface 45*i* (see FIG. 3 and FIG. 4) centered on the second rotational center line 65 and is smaller in radius than the second virtual conical surface 45*i* (see FIG. 3 and FIG. 4). The first and second virtual conical surface 43*i* and 45*i* (see FIG. 3 and FIG. 4) are virtual conical surfaces that approach or contact the first virtual path surface 31 along which the main suction pad 60 moves.

Figure 8:
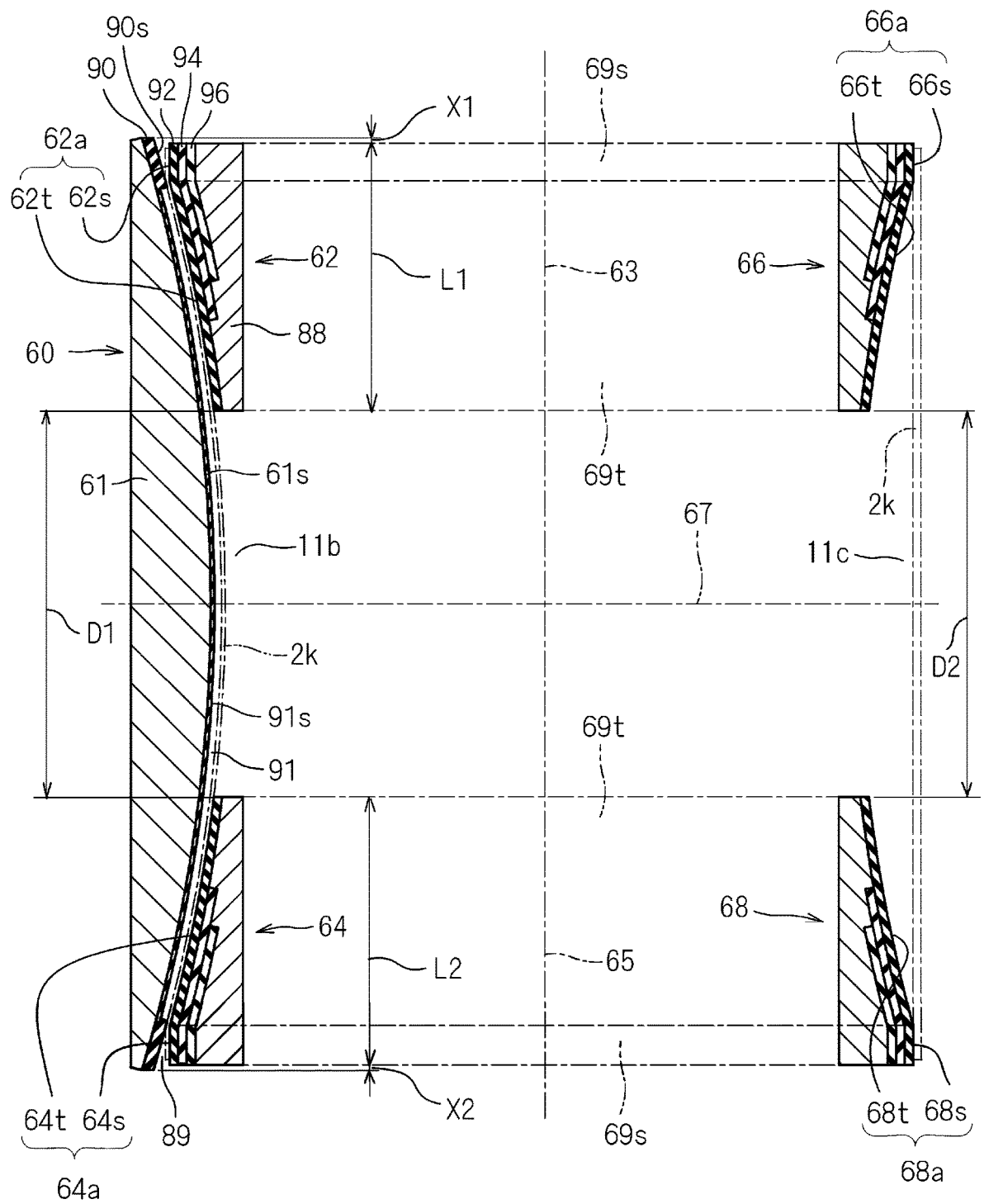
FIG. 8 is a sectional view of principal portions of a second device. (Example 2)
Figure 9:
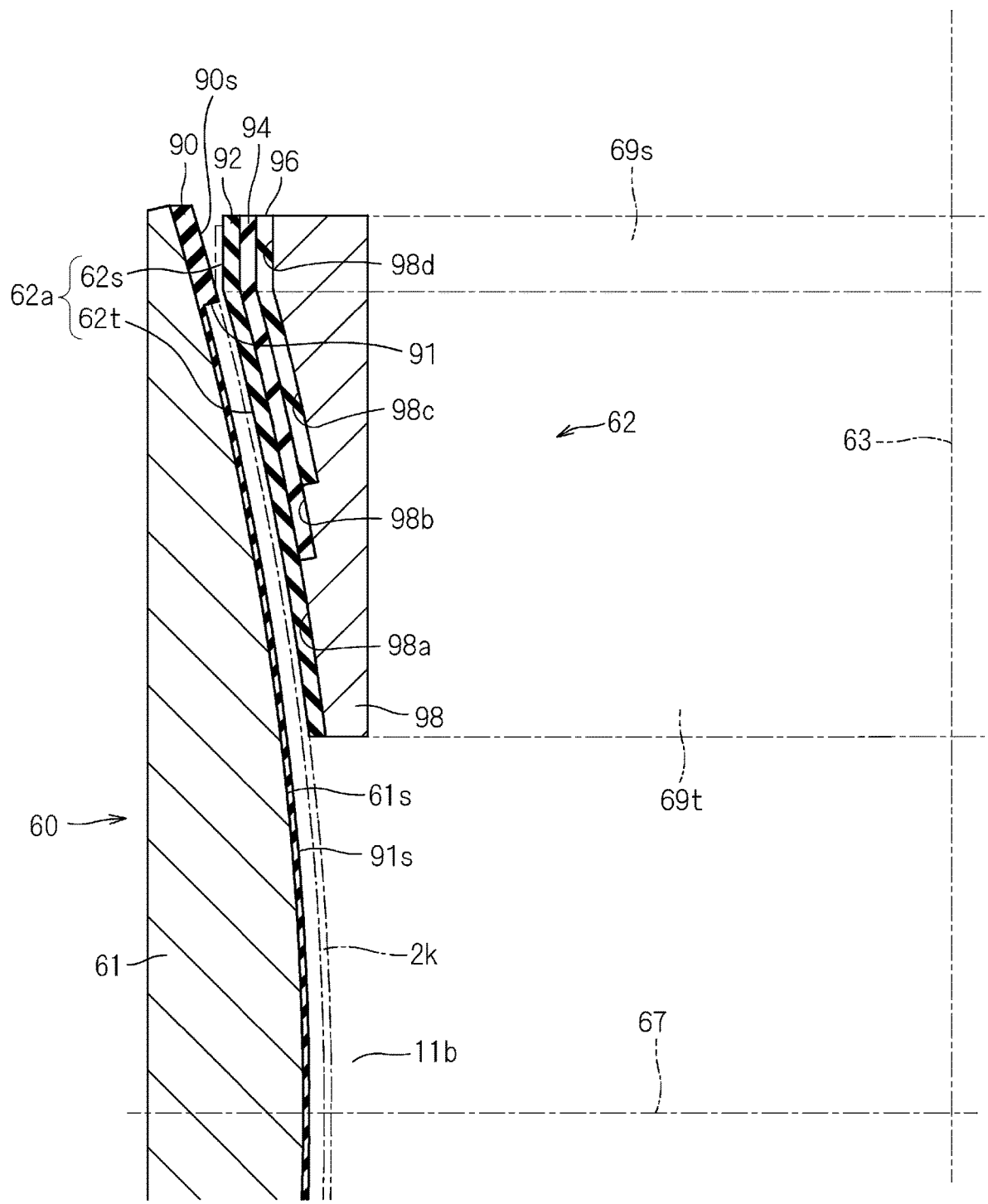
FIG. 9 is an enlarged sectional view of principal portions enlarging a portion of FIG. 8. (Example 2)
Figure 10:
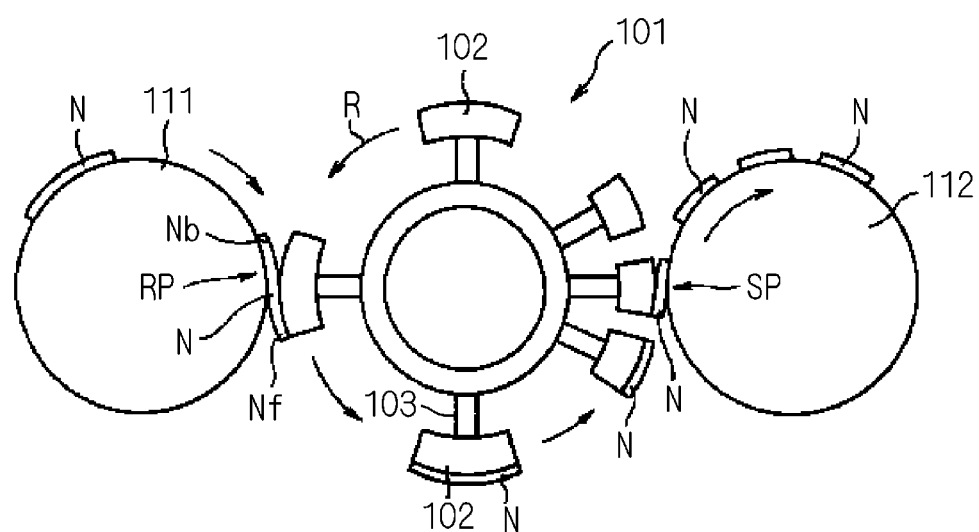
FIG. 10 is a schematic diagram showing an arrangement of an apparatus for manufacturing absorptive article. (Conventional Example 1)

As shown in FIG. 8 and FIG. 9, intersection lines of the first inner suction surfaces 62*t* and 66*t* of the first sub-suction surfaces 62*a* and 66*a* with a plane containing the first rotational center line 63 are arcuate curves that lie along the main suction surfaces 90*s* and 91*s* at the second position 11*b*. Similarly, intersection lines of the second inner suction surfaces 64*t* and 68*t* of the second sub-suction surfaces 64*a* and 68*a* with a plane containing the second rotational center line 65 are arcuate curves that lie along the main suction surfaces 90*s* and 91*s* at the second position 11*b*. Therefore, in comparison to Example 1 where the intersection line of the first inner suction surface of the first sub-suction surface with the plane containing the first rotational center line and the intersection line of the second inner suction surface of the second sub-suction surface with the plane containing the second rotational center line are straight lines, the first and second inner suction surfaces 62*t* and 64*t*; 66*t* and 68*t* of the first and second sub-suction surfaces 62*a* and 64*a*; 66*a* and 68*a* can be made to lie more uniformly along the main suction surfaces 90*s* and 91*s*. Consequently, the constituent element 2*k* can be transferred from the main suction surfaces 90*s* and 91*s* to predetermined positions of the first and second sub-suction surfaces 62*a* and 64*a*; 66*a* and 68*a* more accurately and therefore, the occurrence of wrinkles in the constituent element 2*k* can be prevented further.

By providing the main suction pad 60 with the elastic sheet 90 and providing the first and second sub-suction pads 62 and 64; 66 and 68 with the first elastic sheets 92, the occurrence of wrinkles in the constituent element 2*k* and biting-in of the constituent element 2*k* can be prevented even when the first and second sub-suction surfaces 62*a* and 64*a*; 66*a* and 68*a* are pressed against and put in close contact with the constituent element 2*k* held by the main suction pad 60 when the first and second sub-suction pads 62 and 64; 66 and 68 receive the constituent element 2*k* from the main suction pad 60. Transfer of the constituent element 2*k* from the main suction pad 60 to the first and second sub-suction pads 62 and 64; 66 and 68 is thus stabilized further.

By providing the second and third elastic sheets 94 and 96 of lower hardness than the first elastic sheets 92 below the first elastic sheets 92 in the first and second sub-suction pads 62 and 64; 66 and 68 as shown in FIG. 8 and FIG. 9, the first and second outer suction surfaces 62*s* and 64*s*; 66*s* and 68*s* are made elastically deformable. The first and second outer suction surfaces 62*s* and 64*s*; 66*s* and 68*s* are small in pressing force in a range in which the second and third elastic sheets 94 and 96 deform elastically.

As shown in FIG. 6, there is a case where, when transferring the constituent element 2*k* to the downstream conveying device 50 at the third position 11*c*, the other end 2*t* side of the constituent element 2*k* is superposed on the second continuous body 4 without superposing the one end 2*s* side on the second continuous body 4. Even if in such a case, the first and second outer suction surfaces 62*s* and 64*s*; 66*s* and 68*s* of the first and second sub-suction pads 62 and 64; 66 and 68 press the constituent element 2*k* to the downstream conveying device 50 side at the third position 11*c*, the pressing forces can be made small and therefore the occurrence of wrinkles in the constituent element 2*k* can be prevented. The transfer of the constituent element 2*k* to the downstream device 50 is thereby stabilized further.

Also, even if pressing-in amounts of the first and second outer suction surfaces 62*s* and 64*s*; 66*s* and 68*s* differ according to superposing or not superposing the constituent element 2*k* on the second continuous body 4, the pressing forces of the first and second outer suction surfaces 62*s* and 64*s*; 66*s* and 68*s* can be made to fall within appropriate ranges and therefore, there is no need to individually prepare or individually perform positional adjustment of the first and second sub-suction pads 62 and 64; 66 and 68. Therefore, even if a thickness of the second continuous body 4 or a thickness of the constituent element 2*k* changes due to product type switching, etc., work of exchanging or adjusting the first and second sub-suction pads 62 and 64; 66 and 68 can be made unnecessary or lightened and the first and second sub-suction pads 62 and 64; 66 and 68 can be used as common parts. Work effort and cost can thus be suppressed.

For example, sheets of a silicone sponge are used as the elastic sheets 90, 92, 94, and 96. The elastic sheet 90 of the main suction pad 60 and the first elastic sheets 92 of the sub-suction pads 62 and 64; 66 and 68 contact each other or contact the constituent element 2k and are therefore required to have appropriate friction coefficients and be excellent in wear resistance. The elastic sheet 90 of the main suction pad 60 is required to hold the shape of the recess 91. The first elastic sheets 92 of the sub-suction pads 62 and 64; 66 and 68 are required to deform and form the curved surfaces of the inner suction surfaces 62t and 64t; 66t and 68t and the outer suction surfaces 62s and 64s; 66s and 68s. The second and third elastic sheets 94 and 96 are preferably of low hardness. The less the types of material sheets for forming the elastic sheets 90, 92, 94, and 96, the more preferable. In consideration of the above, preferably, hardness of the elastic sheet 90 of the main suction pad 60 is greater than the hardness of the first elastic sheets 92 of the first and second sub-suction pads 62 and 64; 66 and 68, the hardness of the first elastic sheets 92 of the first and second sub-suction pads 62 and 64; 66 and 68 is greater than that of the second and third sheets 94 and 96 of the sub-suction pads 62 and 64; 66 and 68, and the second and third elastic sheets 94 and 96 of the sub-suction pads 62 and 64; 66 and 68 are of the same hardness and of lower hardness than the hardness of the first elastic sheets 92 of the sub-suction pads 62 and 64; 66 and 68.

The thickness of each of the elastic sheets 90, 92, 94, and 96 does not have to be constant. The number of the elastic sheets 92, 94, and 96 of the sub-suction pads 62 and 64; 66 and 68 should be selected as appropriate.

The apparatus for manufacturing absorptive article of Example 2 is arranged such that at the second position 11b, an area of contact of the constituent element 2k suctioned and held by the main suction pad 60 and the sub-suction surfaces 62a and 64a; 66a and 68a of the sub-suction pads 62 and 64; 66 and 68 becomes greater than that of the apparatus 10 for manufacturing absorptive article of Example 1. Transfer of the constituent element 2k at the second position 11b is thereby stabilized further.

That is, dimensions L1 and L2 (see FIG. 8) in directions of the rotational center lines 63 and 65 of the sub-suction pads 62 and 64; 66 and 68 are larger in comparison to Example 1. In detail, in comparison to Example 1, dimensions in the directions of the rotational center lines 63 and 65 of the outer suction surfaces 62s and 64s; 66s and 68s of the sub-suction pads 62 and 64; 66 and 68 are made smaller, dimensions in the directions of the rotational center lines 63 and 65 of the inner suction surfaces 62t and 64t; 66t and 68t of the sub-suction pads 62 and 64; 66 and 68 are made greater, the space D1 (see FIG. 8) between mutually adjacent sub-suction pads 62 and 64; 66 and 68 is made smaller, and distances X1 and X2 (see FIG. 8) between respective ends of the main suction pad 60 and outer ends of the mutually adjacent sub-suction pads 62 and 64; 66 and 68 are made smaller.

Also, in the apparatus for manufacturing absorptive article of Example 2, the rotating drum 34 (see FIG. 1) of the first device 30 (see FIG. 1) and the first virtual path surface 31 (see FIG. 1) along which the main suction surfaces 90s and 91s of the main suction pad 60 moves may be made larger than those of Example 1. Thereby, the main suction surfaces 90s and 91s of the main suction pad 60 are smaller in curvature and closer to planes in comparison to Example 1. Consequently, the manufacturing apparatus for absorptive body of Example 2 is made smoother in transfer of the constituent element 2k from the upstream device to the first device at the first position and transfer of the constituent element 2k from the first device to the second device at the second position than the manufacturing apparatus for absorptive body of Example 1.

CONCLUSION

As described above, the occurrence of wrinkles in the constituent element of the absorptive article when transferring the constituent element to the downstream conveying device can be suppressed. The occurrence of wrinkles during transfer can be suppressed even when an elastic member is disposed in the constituent element.

The present invention is not restricted to the embodiments described above and can be implemented upon applying various modifications.

For example, although cases where the first and second virtual path surfaces are cylindrical were given as examples, the first and/or second virtual path surface may be conical instead.

REFERENCE SIGNS LIST

2a,2b end portion
2k constituent element
2a, 2b end portion
6 absorptive article
10 apparatus for manufacturing absorptive article
11a first position
11b second position
11c third position
20 upstream conveying device
31 first virtual path surface
31x first reference center line
32 main suction pad
32a one end
32b other end
32s main suction surface
41 second virtual path surface
41x second reference center line
42 first sub-suction pad
42a first sub-suction surface
42m first opposing portion
42s first outer suction surface
42t first inner suction surface
42x first rotational center line
43i first virtual conical surface
43j first virtual cylindrical surface
44 second sub-suction pad
44a second sub-suction surface
44m second opposing surface
44s second outer suction surface
44t second inner suction surface
44x second rotational center line
45i second virtual conical surface
45j second virtual cylindrical surface
46 first sub-suction pad
46a first sub-suction surface
46s first outer suction surface
46t first inner suction surface
46x first rotational center line
48 second sub-suction pad
48a second sub-suction surface
48s second outer suction surface
48t second inner suction surface
48x second rotational center line
50 downstream conveying device 60 main suction pad
62 first sub-suction pad
62a first sub-suction surface
62s first outer suction surface
62t first inner suction surface
63 first rotational center line
64 second sub-suction pad
64a second sub-suction surface
64s second outer suction surface
64t second inner suction surface
65 second rotational center line
66 first sub-suction pad
66s first outer suction surface
66t first inner suction surface
68 second sub-suction pad
68a second sub-suction surface
68s second outer suction surface
68t second inner suction surface
70 intersection
80 controller
90s, 91s main suction surface
D1, D2 space

The invention claimed is:

1. An apparatus for manufacturing absorptive article that receives a constituent element of an absorptive article from an upstream conveying device and after changing an orientation of the constituent element during conveying, transfers the constituent element to a downstream conveying device, the apparatus for manufacturing absorptive article comprising:
a main suction pad having a main suction surface curved to an arcuate surface shape between one end and another end and disengageably suctioning the constituent element, the main suction surface passing a first position and a second position by moving along a cylindrical or conical first virtual path surface centered on a first reference center line and in a circumferential direction of the first virtual path surface, the first virtual path surface being adjacent to the upstream conveying device at the first position, a reference direction connecting the one end and the other end of the main suction surface changing in orientation with respect to the circumferential direction of the first virtual path surface while the main suction surface moves, the reference direction being parallel to the circumferential direction of the first virtual path surface when the main suction surface passes the first position, and the reference direction being perpendicular to the circumferential direction of the first virtual path surface when the main suction surface passes the second position;
a first sub-suction pad having a first sub-suction surface disengageably suctioning a portion of the constituent element, the first sub-suction surface passing the second position and a third position by moving around a second reference center line and along a cylindrical or conical second virtual path surface centered on the second reference center line, the second virtual path surface being adjacent to the first virtual path surface at the second position and being adjacent to the downstream conveying device at the third position; and
a second sub-suction pad having a second sub-suction surface disengageably suctioning another portion of the constituent element, the second sub-suction surface passing the second position and the third position at the same time as the first sub-suction surface by moving around the second reference center line and along the second virtual path surface while being aligned with the first sub-suction surface with a space therebetween,
wherein at the second position, the main suction surface of the main suction pad mutually approaches or contacts the first sub-suction surface of the first sub-suction pad and the second sub-suction surface of the second sub-suction pad, and the space between the first sub-suction surface and the second sub-suction surface when the first sub-suction surface and the second sub-suction surface pass the third position becomes greater than the space between the first sub-suction surface and the second sub-suction surface when the first sub-suction surface and the second sub-suction surface pass the second position, and
wherein the first sub-suction surface of the first sub-suction pad includes
a first inner suction surface being a curved surface lying along a third virtual conical surface that is internally tangent to a first virtual conical surface contacting or approaching the first virtual path surface and being centered on the first rotational center line and is smaller in radius than the first virtual conical surface, and
a first outer suction surface being a portion of a cylindrical curved surface that is internally tangent to a first virtual cylindrical surface centered on the first rotational center line, the first virtual cylindrical surface being adjacent to a large diameter side of the first virtual conical surface, and is smaller in radius than the first virtual cylindrical surface, and
the second sub-suction surface of the second sub-suction pad includes
a second inner suction surface being a curved surface lying along a fourth virtual conical surface that is internally tangent to a second virtual conical surface contacting or approaching the first virtual path surface and being centered on the second rotational center line, the second virtual conical surface being such that a small diameter side of the second virtual conical surface opposes a small diameter side of the first virtual conical surface, and is smaller in radius than the second virtual conical surface, and
a second outer suction surface being a portion of a cylindrical curved surface that is internally tangent to a second virtual cylindrical surface centered on the second rotational center line, the second virtual cylindrical surface being adjacent to a large diameter side of the second virtual conical surface, and is smaller in radius than the second virtual cylindrical surface.

2. The apparatus for manufacturing absorptive article according to claim 1, wherein
the first virtual path surface and the second virtual path surface are cylindrical,
the first reference center line and the second reference center line are parallel to each other,
the first sub-suction pad rotates around a first rotational center line,
the second sub-suction pad rotates around a second rotational center line,
a portion of the first rotational center line further to the second sub-suction pad side than a first opposing portion opposing the first sub-suction pad and a portion of the second rotational center line further to the first sub-suction pad side than a second opposing portion opposing the second sub-suction pad intersect at an intersection and an angle at the second position side of angles formed by the first rotational center line and the second rotational center line is not less than 170° but less than 180°, and a portion of the first rotational center line further to the first opposing portion side than the intersection and a portion of the second rotational center line further to the second opposing portion side than the intersection are positioned further to the second position side than a straight line that passes through the intersection and is parallel to the second reference center line.

3. The apparatus for manufacturing absorptive article according to claim 2, further comprising: a controller that is capable of making a first speed when the first sub-suction surface and the second sub-suction surface pass the second position and a second speed when the first sub-suction surface and the second sub-suction surface pass the third position differ.

4. The apparatus for manufacturing absorptive article according to claim 1, further comprising: a controller that is capable of making a first speed when the first sub-suction surface and the second sub-suction surface pass the second position and a second speed when the first sub-suction surface and the second sub-suction surface pass the third position differ.

5. A method for manufacturing absorptive article by which a constituent element of an absorptive article is received from an upstream conveying device and after the constituent element is changed in orientation during conveying, the constituent element is transferred to a downstream conveying device, the method for manufacturing the absorptive article comprising:

a first step in which a main suction surface that is curved to an arcuate surface shape between one end and another end and disengageably suctions the constituent element passes a first position and a second position by moving along a cylindrical or conical first virtual path surface centered on a first reference center line and in a circumferential direction of the first virtual path surface, the first virtual path surface being adjacent to the upstream conveying device at the first position, while the main suction surface moves, a reference direction connecting the one end and the other end of the main suction surface changes in orientation with respect to the circumferential direction of the first virtual path surface, when the main suction surface passes the first position, the main suction surface approaches or contacts the constituent element conveyed by the upstream conveying device and the main suction surface suctions the constituent element in a state where the reference direction and the circumferential direction of the first virtual path surface are parallel to each other, next, while the main suction surface moves to the second position while still suctioning the constituent element, the orientation of the reference direction with respect to the circumferential direction of the first virtual path surface changes, and next, when the main suction surface passes the second position, the reference direction is made perpendicular to the circumferential direction of the first virtual path surface, and a second step in which a first sub-suction surface and a second sub-suction surface pass the second position and a third position at the same time as each other by moving, while being aligned with a space provided mutually therebetween, around a second reference center line and along a cylindrical or conical second virtual path surface centered on the second reference center line, the second virtual path surface being adjacent to the first virtual path surface at the second position and being adjacent to the downstream conveying device at the third position, at the same time as when the main suction surface of the main suction pad passes the second position, the first sub-suction surface and the second sub-suction surface pass the second position, the first sub-suction surface approaches or contacts one end portion at the one end side of the main suction surface among a pair of mutually opposing end portions of the constituent element suctioned by the main suction surface of the main suction pad, the second sub-suction surface approaches or contacts the other end portion at the other end side of the main suction surface, and the first sub-suction surface and the second sub-suction surface suction the end portions of the constituent element, next, the first sub-suction surface and the second sub-suction surface move to the third position while still suctioning the end portions of the constituent element and next, when the first sub-suction surface and the second sub-suction surface pass the third position, the constituent element the end portions of which are suctioned by the first sub-suction surface and second sub-suction surface is made to approach or contact the downstream conveying device and the constituent element is transferred to the downstream conveying device, wherein in the second step, the space between the first sub-suction surface and the second sub-suction surface when the first sub-suction surface and the second sub-suction surface pass the third position is made greater than the space between the first sub-suction surface and the second sub-suction surface when the first sub-suction surface and the second sub-suction surface pass the second position, and wherein the first sub-suction surface of the first sub-suction pad includes a first inner suction surface being a curved surface lying along a third virtual conical surface that is internally tangent to a first virtual conical surface contacting or approaching the first virtual path surface and being centered on the first rotational center line and is smaller in radius than the first virtual conical surface and a first outer suction surface being a portion of a cylindrical curved surface that is internally tangent to a first virtual cylindrical surface centered on the first rotational center line, the first virtual cylindrical surface being adjacent to a large diameter side of the first virtual conical surface, and is smaller in radius than the first virtual cylindrical surface, and the second sub-suction surface of the second sub-suction pad includes a second inner suction surface being a curved surface lying along a fourth virtual conical surface that is internally tangent to a second virtual conical surface contacting or approaching the first virtual path surface and being centered on the second rotational center line, the second virtual conical surface being such that a small diameter side of the second virtual conical surface opposes a small diameter side of the first virtual conical surface, and is smaller in radius than the second virtual conical surface, and a second outer suction surface being a portion of a cylindrical curved surface that is internally tangent to a second virtual cylindrical surface centered on the second rotational center line, the second virtual cylindrical surface being adjacent to a large diameter side of the second virtual conical surface, and is smaller in radius than the second virtual cylindrical surface.

6. The method for manufacturing absorptive article according to claim 5, wherein the first virtual path surface and the second virtual path surface are cylindrical, the first reference center line and the second reference center line are parallel to each other, and in the second step, the first sub-suction pad rotates around a first rotational center line, the second sub-suction pad rotates around a second rotational center line, a portion of the first rotational center line further to the second sub-suction pad side than a first opposing portion opposing the first sub-suction pad and a portion of the second rotational center line further to the first sub-suction pad side than a second opposing portion opposing the second sub-suction pad intersect at an intersection and an angle at the second position side of angles formed by the first rotational center line and the second rotational center line is not less than 170° but less than 180°, and a portion of the first rotational center line further to the first opposing portion side than the intersection and a portion of the second rotational center line further to the second opposing portion side than the intersection are positioned further to the second position side than a straight line that passes through the intersection and is parallel to the second reference center line.

7. The method for manufacturing absorptive article according to claim 5, wherein in the second step, a first speed when the first sub-suction surface and the second sub-suction surface pass the second position and a second speed when the first sub-suction surface and the second sub-suction surface pass the third position differ.

8. The method for manufacturing absorptive article according to claim 6, wherein in the second step, a first speed when the first sub-suction surface and the second sub-suction surface pass the second position and a second speed when the first sub-suction surface and the second sub-suction surface pass the third position differ.

* * * * *